United States Patent
Desjardins et al.

(10) Patent No.: US 12,036,012 B2
(45) Date of Patent: Jul. 16, 2024

(54) SENSOR FOR MEASURING A FLOW OF A FLUID

(71) Applicant: UCL BUSINESS LTD, London (GB)

(72) Inventors: Adrien Desjardins, London (GB); Malcolm Finlay, London (GB); Ioannis Papakonstantinou, London (GB); Charles Alexander Mosse, London (GB); Joanna M. Coote, London (GB); Sacha Noimark, London (GB); Erwin Alles, London (GB)

(73) Assignee: UCL BUSINESS LTD, London (GB)

( * ) Notice: Subject to any disclaimer, the term of this patent is extended or adjusted under 35 U.S.C. 154(b) by 957 days.

(21) Appl. No.: 16/963,793

(22) PCT Filed: Jan. 22, 2019

(86) PCT No.: PCT/GB2019/050163
§ 371 (c)(1),
(2) Date: Jul. 21, 2020

(87) PCT Pub. No.: WO2019/142006
PCT Pub. Date: Jul. 25, 2019

(65) Prior Publication Data
US 2021/0052173 A1      Feb. 25, 2021

(30) Foreign Application Priority Data

Jan. 22, 2018    (GB) ...................... 1800997

(51) Int. Cl.
*A61B 5/026*      (2006.01)
*A61B 5/00*       (2006.01)
*A61B 90/30*      (2016.01)

(52) U.S. Cl.
CPC .......... *A61B 5/0261* (2013.01); *A61B 5/6852* (2013.01); *A61B 5/7278* (2013.01);
(Continued)

(58) Field of Classification Search
CPC ... A61B 5/0261; A61B 5/6852; A61B 5/7278; A61B 2090/306; A61B 2503/40
See application file for complete search history.

(56) References Cited

U.S. PATENT DOCUMENTS 5,208,650 A  *  5/1993  Giallorenzi ............. G01F 1/661
                                                     250/227.27
5,601,611 A      2/1997  Fayram et al.
(Continued)

FOREIGN PATENT DOCUMENTS

CN    108603774 A  *  9/2018   ......... G01D 5/35312
GB    2542284 A        3/2017
(Continued)

OTHER PUBLICATIONS

Roman V. Kuranov et al: "Depth-resolved blood oxygen saturation measurement by dual-wavelength photothermal (DWP) optical coherence tomography", Biomedical Optics Express, vol. 2, No. 3, Mar. 1, 2011 (Mar. 1, 2011), p. 491, XP055598076, United States, ISSN: 2156-7085, DOI: 10.1364/BOE.2.000491 section 2; figures 1-2, p. 502, the whole document.
(Continued)

*Primary Examiner* — Oommen Jacob
(74) *Attorney, Agent, or Firm* — Harness, Dickey & Pierce, P.L.C.

(57)   ABSTRACT

A sensor is provided for measuring a flow of a fluid in a physiological environment, such as within a vessel of a human or animal subject. The sensor comprises an interrogation light guide extending from a proximal end to a distal end of the sensor. The interrogation light guide is configured to transmit interrogation light to, and receive reflected interrogation light from, the distal end of the sensor. The sensor further comprises an excitation light guide configured to transmit excitation light to the distal end of the sensor. The excitation light is provided for heating the fluid (directly or (Continued)

indirectly). The sensor further comprises a sensing element located at the distal end of the sensor. The sensing element comprises at least two etalons for reflecting interrogation light back along the interrogation light guide towards the proximal end of the sensor. Each etalon has a respective optical path length and further has at least one reflective surface external to the interrogation light guide. The sensing element is configured to be in thermal contact with the fluid such that the optical path length of at least one etalon is dependent on a temperature of the fluid. The reflected interrogation light forms an interferogram which is dependent on the optical path lengths of the respective etalons.

20 Claims, 12 Drawing Sheets

(52) U.S. Cl.
CPC ..... *A61B 2090/306* (2016.02); *A61B 2503/40* (2013.01); *A61B 2560/0223* (2013.01); *A61B 2562/0233* (2013.01)

(56) References Cited

U.S. PATENT DOCUMENTS

| | | | | |
|---|---|---|---|---|
| 5,612,778 | A * | 3/1997 | Hall | G01D 5/35303 |
| | | | | 356/477 |
| 5,785,657 | A | 7/1998 | Breyer et al. | |
| 6,445,939 | B1 * | 9/2002 | Swanson | G02B 6/2552 |
| | | | | 385/33 |
| 6,671,055 | B1 | 12/2003 | Wavering et al. | |
| 9,557,344 | B2 | 1/2017 | Tam et al. | |
| 9,995,628 | B1 * | 6/2018 | Han | G01K 11/3206 |
| 10,359,316 | B1 * | 7/2019 | Han | G01J 5/0853 |
| 10,869,603 | B2 * | 12/2020 | Millett | A61B 5/0035 |
| 2002/0159671 | A1 * | 10/2002 | Boyd | G01L 9/0079 |
| | | | | 385/12 |
| 2005/0151975 | A1 * | 7/2005 | Melnyk | G01B 9/02023 |
| | | | | 356/480 |
| 2006/0257071 | A1 * | 11/2006 | Bise | G02B 6/03611 |
| | | | | 385/29 |
| 2007/0006663 | A1 | 1/2007 | Zerwekh et al. | |
| 2008/0058908 | A1 * | 3/2008 | Bornstein | A61C 19/063 |
| | | | | 607/93 |
| 2008/0154141 | A1 | 6/2008 | Shuros et al. | |
| 2008/0188843 | A1 * | 8/2008 | Appling | A61B 18/24 |
| | | | | 606/15 |
| 2010/0049060 | A1 | 2/2010 | Pacesetter | |
| 2012/0203113 | A1 | 8/2012 | Skerl et al. | |
| 2013/0014577 | A1 | 1/2013 | Tam et al. | |
| 2014/0168659 | A1 * | 6/2014 | Suri | G01K 11/3206 |
| | | | | 356/480 |
| 2014/0243688 | A1 * | 8/2014 | Caron | A61B 5/026 |
| | | | | 600/478 |
| 2014/0318273 | A1 * | 10/2014 | Dong | G01K 11/3206 |
| | | | | 374/161 |
| 2018/0058949 | A1 * | 3/2018 | Dong | G01D 5/268 |
| 2021/0052173 | A1 * | 2/2021 | Desjardins | A61B 5/0215 |

FOREIGN PATENT DOCUMENTS

| | | | | |
|---|---|---|---|---|
| JP | | 2012501703 A | 1/2012 | |
| JP | | 2014523757 A | 9/2014 | |
| JP | | 2015501184 A | 1/2015 | |
| WO | WO-2008067079 | A2 | 6/2008 | |
| WO | WO-2013061280 | A1 | 5/2013 | |
| WO | WO-2016086856 | A1 | 6/2016 | |
| WO | WO-2016113543 | A1 | 7/2016 | |
| WO | WO-2016183321 | A1 * | 11/2016 | ........... G01B 11/161 |
| WO | WO-2016196954 | A1 | 12/2016 | |

OTHER PUBLICATIONS

Xia Wenfeng et al: "Fiber optic photoacoustic probe with ultrasonic tracking for guiding minimally invasive procedures", Progress in Biomedical Optics and Imaging, SPIE—International Society for Optical Engineering, Bellingham, WA, US, vol. 9539, Jul. 16, 2015 (Jul. 16, 2015), pp. 95390K-95390K, XP060056426, ISSN: 1605-7422, DOI: 10.1117/12.2182647, ISBN: 978-1-5106-0027-0, abstract, section 2; figure 1.

Yelderman, MD., Mark, "Continuous measurement of Cardiac Output with the Use of Stochastic System Identification Techniques", J. Clin Monit, 1990;6 pp. 322-332.

International Search Report and Written Opinion of the International Searching Authority issued in PCT/GB2019/050163, mailed Jul. 3, 2019; ISA/EP.

Search Report Under Section 17 issued in GB-1800997.7, date of search, Oct. 8, 2018.

* cited by examiner

SENSOR FOR MEASURING A FLOW OF A FLUID

CROSS REFERENCE TO RELATED APPLICATIONS

This application is a U.S. National Phase Application under 35 U.S.C. 371 of International Application No. PCT/GB2019/050163 filed on Jan. 22, 2019, which claims the benefit of priority from Great Britain Patent Application No. 1800997.7 filed on Jan. 22, 2018. The entire disclosures of all of the above applications are incorporated herein by reference.

FIELD

The present application relates to a sensor for measuring a flow of a fluid in a physiological environment, such as within a vessel of a human or animal subject.

BACKGROUND

The flow of fluids in vessels within the human body yields physiological parameters that are clinically important for diagnostic and therapeutic purposes. For instance, measurements of blood flow in the coronary arteries can be used to assess the severity of a stenosis and thereby to assist with a decision about whether to place a stent. Similarly, measurement of cardiac blood flow is extremely valuable for monitoring a critically ill patient or during major surgery. As an example, the effective stroke volume may be determined from the blood flow in the aorta, and based on the variation of the aortal flow over time, a conclusion may be drawn concerning the rate of cardiac insufficiency, the haemodynamic effects of arrhythmia, possible treatment parameters, and/or the vascular characteristics of the aorta. As another example, the blood flow in the renal arteries is an important parameter for the diagnosis and treatment of renal insufficiency. A complete assessment and appreciation of the haemodynamics of a blood vessel requires knowledge of both pressure and fluid dynamics. An ideal device for providing these measurements would be small in lateral extent, provide highly accurate data which are stable and robust, be inexpensive to manufacture, and immune to interference such as electromagnetic interference. Currently available measurement devices fall short of this ideal for various reasons.

Fluid flow can be measured using different parameters, such as the volumetric flow rate, or the speed of the fluid in a particular direction and at a particular location. Various methods are known for measuring the blood flow in blood vessels. Invasive methods, which involve positioning a medical device with a sensor within a vessel, may be utilised to achieve high accuracy, but such methods generally require a specific manual procedure in order to acquire precise measurements; accordingly, such measurements have largely remained outside of standard clinical practice.

Acoustic Doppler flow measurements, for instance those implemented in invasive medical devices such as guidewires, provide time-resolved flow speed measurements. However, these measurements vary with the angle between the central axis of the acoustic beam and the direction of blood flow, which is generally difficult to control. The acquisition of such acoustic Doppler measurements in invasive medical devices therefore involves precise and stable alignment of the acoustic beam with the blood vessel being investigated, and slight deviations or fluctuations may result in measurement errors.

Acoustic flow measurement methods based on ultrasound travel time are also used. These methods typically involve two acoustic transducers which are externally applied to the blood vessel in an offset manner. A disadvantage of this approach is the requirement for precise knowledge of the time-of-flight acoustic distance between the transducers.

Related acoustic flow methods in which the acoustic beam extends in a perpendicular direction relative to the vessel are also known. For example, in U.S. Pat. No. 5,785,657, the autocorrelation function (ACF) of the received signal is determined for this purpose, and the minima of the ACF are used to determine the time required for the scattered particles to cross the measured volume. If the dimensions of the measured volume are precisely known, the velocity and thus the flow rate of the particles may be determined. A disadvantage of this type of method is that the measured volume must be precisely known and stable.

Also known are optical methods based on the principle of the laser Doppler anemometer, and related optical methods, such as those disclosed in U.S. Pat. No. 5,601,611, which use computational methods to directly evaluate signals backscattered by blood components in order to obtain information about blood flow rate. The use of micro-hair sensors for blood flow measurement is also known. Micro-hairs or banners, manufactured using MEMS technology, project into the blood flow and are bent or deflected by the moving medium; see US 2008/0154141 for an example. A disadvantage of this type of arrangement is that clots may form on the foreign bodies protruding into the blood flow. In addition, the micro-hairs or banners may become agglutinated or encapsulated, thereby losing their functionality.

Also known are methods that use a photoplethysmogram (PPG) for determining surrogate parameters for blood pressure and blood flow. For example, the PPG sensor described in US 2010/049060 is located on the housing of an implantable medical device (IMD), such as in the header thereof. Surrogate parameters for blood pressure and the blood flow may be determined based on the PPG. A disadvantage of such methods is that they are based on assumed blood flow models and parameters which are not precisely known, and which are subject to time-related and individual fluctuations. In addition, secondary effects such as changes in the vascular tone (for example) may have a significant influence on the determination of these surrogate parameters.

The use of optical reflections at two locations along a vessel to allow calculation of noise in reflected light, and the subsequent cross-correlation of such noise to permit time-of-flight calculations to be performed for the flow, is described in US2012-0203113A1. A disadvantage of this approach is that these calculations involve determining a statistical correlation between very small signals, which may introduce substantial error and requires high technical complexity. Such devices also utilise several transmitters and receivers, which limits their use in small vessels.

Thermal flow measurement methods, including classical methods of hot-wire anemometry, represent an important alternative to Doppler method. Thermal anemometric methods such as thermo-dilution measurements are also common, although current implementations are somewhat cumbersome and prone to complications, as they involve injections of fluid such as cold saline into the vessel.

It is also known to use sequential Fibre-Bragg gratings to monitor temperature changes at multiple locations within an optical fibre, and thereby provide flow measurements following a temperature change upstream. However, such Fibre-Bragg gratings are costly to manufacture and are also insensitive to pressure changes within physiological ranges.

Surrogate measurements of flow may be obtained with pressure measurements, for instance as implemented with fractional flow reserve (FFR) within coronary arteries. Measuring absolute and relative pressure within a coronary artery is an important diagnostic parameter, allowing the calculation of FFR. However, FFR is known to be an imperfect measure of flow as it relies on many assumptions that are not always accurate. Direct flow measurements generally provide more accurate parameters with which to make diagnostic decisions or to guide therapies, particularly when considered as a complement to measured pressures within a vessel. Moreover, current invasive pressure sensors are relatively complex to manufacture, especially if such sensors have to satisfy strict requirements for pressure sensitivity and immunity to drift.

SUMMARY

The invention is defined in the appended claims.

A sensor is provided for measuring a flow of a fluid in a physiological environment, such as within a vessel of a human or animal subject. The sensor comprises an interrogation light guide extending from a proximal end to a distal end of the sensor. The interrogation light guide is configured to transmit interrogation light to, and receive reflected interrogation light from, the distal end of the sensor. The sensor further comprises an excitation light guide configured to transmit excitation light to the distal end of the sensor. The excitation light is provided for heating the fluid (directly or indirectly). The sensor further comprises a sensing element located at the distal end of the sensor. The sensing element comprises at least two etalons for reflecting interrogation light back along the interrogation light guide towards the proximal end of the sensor. Each etalon has a respective optical path length. At least one etalon (or, in some examples, each etalon) has at least one reflective surface external to the interrogation light guide. The sensing element is configured to be in thermal contact with the fluid such that the optical path length of at least one etalon is dependent on a temperature of the fluid. The reflected interrogation light forms an interferogram which is dependent on the optical path lengths of the respective etalons.

The present invention also provides a method as described herein for using such a sensor.

There are many medical fields where the acquisition or measurement of high-fidelity data regarding pressure, flow, or location from within the body is beneficial. Such measurements may be used for diagnosis or to guide surgical or minimally invasive interventional treatments, such as assessing the physiological significance of a lesion in a coronary artery, the function of a heart valve, total or fractional cardiac output or perfusion of one or more vascular beds, or determining the pressure within the cerebrospinal space. The measurement data acquired can be subsequently used to guide the placing of a stent or valve repair, or inform other medical treatments.

A sensing device (sensor) as described herein can perform high-quality, multi-parametric measurements from a highly-miniaturised probe without electronic components at the distal end. Such a device avoids various drawbacks of known methods of performing minimally-invasive pressure or flow measurements, such as indirect measurements with slow frequency response (obtained via bulky fluid-columns), miniaturised electronic sensors having complex manufacturing and connectorisation requirements, etc. Such a fibre optic sensor supports both pressure and flow measurements from the use of a single interrogation light guide extending along the sensor, and so offers a compact and effective sensor that can be readily integrated into an invasive medical device.

In further examples, a sensor for measuring a flow of a fluid in a physiological environment can comprise at least one sensing element, such that the sensor comprises:
an interrogation light guide extending from a proximal end to a distal end of the sensor, the interrogation light guide being configured to transmit interrogation light to, and receive reflected interrogation light from, the distal end of the sensor;
an excitation light guide configured to transmit excitation light to the distal end of the sensor, wherein the excitation light is provided for heating the fluid; and
at least one sensing element located at the distal end of the sensor, the at least one sensing element comprising at least two etalons for reflecting interrogation light back along the interrogation light guide towards the proximal end of the sensor, each etalon having a respective optical path length and having at least one reflective surface external to the interrogation light guide;
wherein the at least one sensing element is configured to be in thermal contact with the fluid such that the optical path length of at least one etalon is dependent on a temperature of the fluid, and wherein the reflected interrogation light forms an interferogram which is dependent on the optical path lengths of the respective etalons.

BRIEF DESCRIPTION OF THE DRAWINGS

Various implementations of the invention will now be described in detail by way of example only with reference to the following drawings.

Figure 1:
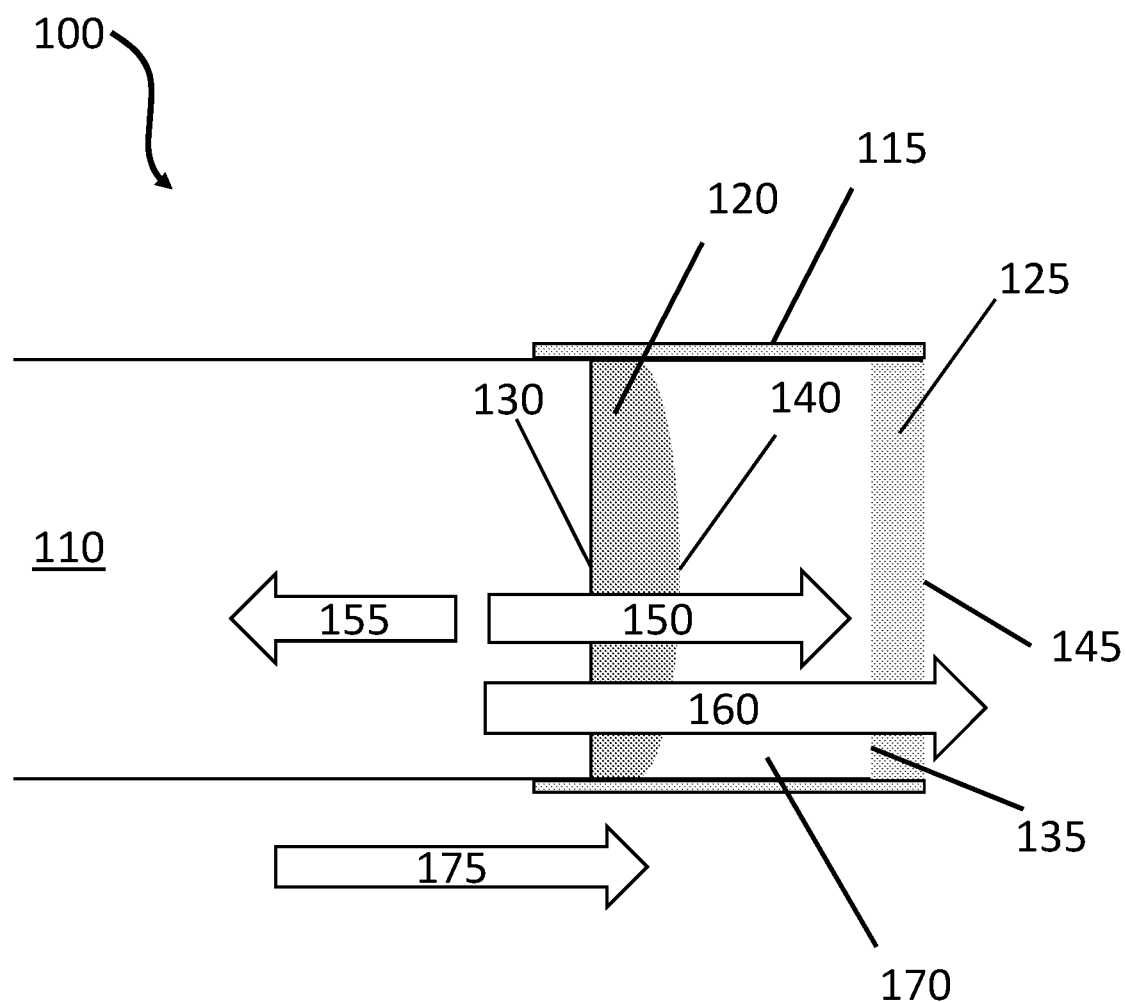
FIG. 1 is a schematic diagram of an example of a sensor as described herein, the sensor including an optical fibre having a coating and a membrane located in a capillary extending from the optical fibre.

Note that in the Figures, like components in different implementations are indicated by a consistent reference number across different figures. In the interest of conciseness, the description of such like components is not necessarily repeated for each figure, but it will be appreciated that the description of such a component in respect of one figure can generally be applied to that same component in other figures.

DETAILED DESCRIPTION

Described herein is a sensing device which may be used as an implanted (inserted) sensor for measuring physiological parameters within the body. One implementation of such a device may be used to perform flow and pressure measurements within a living body, such as for determining the flow speed or volumetric flow rate of the blood in a blood vessel, or the flow of urine within the urinary tract.

One example of such a sensor (or sensing device) includes a light guide configured to transmit interrogation light of multiple wavelengths to a distal end of the sensor, and to receive reflected interrogation light which forms one or more interferograms. A light guide is also provided to transmit excitation light to the distal end of the sensor for heating a medium or fluid in which the sensor is located. The sensor further comprises a series of (partially) reflective surfaces at the distal end of the sensor, at least one of which is configured to be in thermal contact with the medium. The interrogation light reflected from these surfaces contains (encodes) one or more interferograms which are dependent on the optical path lengths of etalons formed from pairs of the reflective surfaces.

This use of fibre optic technologies supports the provision of highly compact sensors having a sufficiently small size (diameter) and flexibility to be suitable for introduction into a pressure guidewire or other intracoronary device (for example). These technologies also have the advantage of low manufacturing costs based on established industrial processes.

For a sensing device containing three partially reflective surfaces, there are three etalons (each formed from a different pairing of the three reflective surfaces). Changes in the position or shape of the reflective surfaces, and hence in the optical path lengths of these etalons, may result from pressure and/or temperature. For instance, an etalon that comprises two reflective surfaces separated by a gas cavity will decrease in optical path length if there is an increase in the (external) pressure of the flow medium, since this pressure increase will cause a compression of the gas cavity. Likewise, the optical path length of an etalon that has a polymer as a reflective surface may increase with temperature due to thermal expansion of the polymer. Changes in both pressure and temperature of the fluid can therefore be measured based on changes in the optical path lengths of the multiple etalons. The different etalons have differing sensitivities to changes in pressure and temperature, thereby allowing measured changes in pressure to be decoupled from measured changes in temperature (and vice versa). The flow speed of the fluid can then be determined, for example, from the measured change or variation of temperature with time, as described in more detail below.

Each etalon can be considered as contributing a component to the interferogram in the reflected interrogation light. The contributions from the different (respective) etalons may be distinguished based on the interferogram frequency according to the (known) principle of Fourier-Domain optical coherence tomography (FD-OCT), which exploits a linear relationship between the optical path length and a higher interferogram frequency.

With conventional light sources, optical path lengths are typically resolved to a resolution of 2 to 20 µm. However, the (known) technique of Doppler FD-OCT can be used to measure much smaller changes in the optical path lengths of the etalons, e.g. as resulting from physiological changes in external pressure and temperature. In Doppler FD-OCT, the phase of the Fourier-transformed interferogram with a frequency corresponding to a particular etalon is compared with the phase from the same etalon obtained at a different point in time. Differences in the phase are linearly related to the change in etalon path length, which may then be resolved to sub-nanometre resolution.

As described in more detail below, the interference pattern from a given etalon shifts slightly in frequency according to the optical path length of the etalon. The interrogation light for such a sensing device is provided over a frequency range to allow this frequency shift (and hence the optical path length of the etalon) to be determined. In some implementations therefore, the interrogation light may be generated by a broadband optical source (and/or by a combination of multiple monochromatic sources), in which case a spectrometer may be conveniently used for measuring the resulting interferogram. Another possibility for generating the interrogation light is to use a wavelength-swept monochromatic optical source, which then allows a photodetector to be employed for the measurement of the interferogram (since in effect, the frequency range is now encoded onto the time domain). This latter implementation may (re)use optical hardware components, in particular the wavelength-swept monochromatic optical source and photodetector, from an optical coherence tomography system (OCT).

Flow measurements may be performed with such a sensing device by relating measured changes in temperature at the distal end of the sensor to the application by the excitation light of heat to the medium (fluid). In one mode of operation, the excitation light is used to heat the medium directly at the distal end of the sensor. This causes a rise in temperature of the sensor, which in turn causes a change in the optical path length of one or more etalons, which can then be detected via the interrogation light. When heating is applied with excitation light, the resulting rise in temperature at the distal end of the sensor is dependent on the volumetric flow rate: the rise in temperature is typically larger for smaller volumetric flow rates, as heat is carried away from the location where it is applied at a smaller rate. Likewise, for a transitory (e.g. pulse) input of excitation light, the time variation of the rise and fall in temperature of the medium at the distal end of the sensor is dependent on the flow rate. This mode of operation may involve predetermined calibrations (for example, derived by modelling or empirically) in order to obtain the flow rate from the temperature response to the input excitation light.

In another mode of operation, a brief pulse of excitation light (typically much shorter than the cardiac cycle for physiological applications) is used to produce transient heating of the medium at a first position with a known, proximal distance offset from the distal end. With the sensor configured so that the distal end is downstream from the first position, the heated medium will flow from the first position to the distal end. When the heated medium arrives at the distal end, the increased temperature of the fluid changes the optical path length of one or more etalons. In this mode, time-gated flow measurements may be performed directly, without modelling, based on (i) the distance from the first position to the distal end, which is known from the design of the sensor, and (ii) the measured time interval between the pulse of excitation light and the detected rise in temperature at the distal end of the medical device.

Other modes of operation for the sensing device include the use excitation light with different characteristics, for instance pulses that are extended in time, e.g. in vascular applications they could be longer than a cardiac cycle, or that incorporate intensity modulations, e.g. with sinusoidal functions, chirped functions, or a pseudorandom sequence (J Clin Monit. 1990 October; 6(4):322-32). In some implementations, the pulses of excitation light may be time-gated relative to an electrocardiogram (ECG) measurement, a respiratory measurement, or some other periodic (electrical) biological signal, such as an electromyogram. In some implementations, the intensity of excitation light is dependent on a temperature measurement of the fluid or sensor or of the medical device in which the sensor is integrated (for example, to avoid over-heating of the fluid).

The optical absorption spectrum of the flowing medium is typically wavelength-dependent. For instance, water and lipids are known to have prominent optical absorption peaks in the near-infrared wavelength region, and hemoglobins are known to have prominent optical absorption peaks in the visible and near-infrared wavelength regions. By varying the wavelength of the excitation light, the resulting measured temperature changes can be used to obtain information about the composition of the flowing medium and/or to vary the spatial region in the medium (fluid) in which heating is applied. Light with different excitation light wavelengths may be provided sequentially or concurrently; the latter could be effected, for instance, by modulating excitation light with different frequencies according to the wavelength and then demodulating the measured temperature changes. With a suitable choice of excitation wavelength, blood oxygen saturation measurements may be performed in this manner. In many clinical contexts, it is important to obtain information about the locations of medical devices that are positioned within the body. One known method of this is ultrasonic tracking, in which an ultrasound receiver or transmitter integrated in the medical device allows for communication with an ultrasound imaging probe—in some cases using a fibre optic hydrophone having a high-finesse cavity formed by a pair of highly reflective surfaces. In the context of the sensor described herein, one or more of the etalons in the sensor can be configured to be both low-finesse at the wavelength range of the interrogation light and high-finesse at a different wavelength range. Such wavelength characteristics can be achieved, for example, by using dichroic mirrors, which may be applied to the sensor using a thin film coating process. Using wavelength-division multiplexing, light at this different wavelength range can then be used to receive ultrasound signals concurrently with measurements of flow and pressure. The received ultrasound signals are then also encoded in the interrogation light having the different wavelength, and may be extracted and processed to give positional information by a suitable analysis system located at the proximal end of the sensor.

In such an implementation, two reflective surfaces in the sensor may have a low reflectivity (typically in the range of 1-5%) at the wavelength range of interrogation light to form the low finesse cavity, while the same surfaces may have a high reflectivity (typically greater than 70%) at a second wavelength range to form the high finesse cavity. These optical characteristics can be provided, for example, by providing a suitable dielectric coating on the reflecting surfaces.

In some implementations, a membrane is located at the distal tip of one or more optical fibres of the sensor (sensing device) described herein. Examples of a suitable material for the membrane are the polymer polydimethylsiloxane (PDMS), or a composite material, such as a polymer coated with a barrier film such as aluminium oxide. Optical detection of the deformation of this membrane can be used to perform the flow measurements. For example, the membrane may have two reflective surfaces: one on the proximal side and one on the distal side, while the distal end of the optical fibre may provide a third reflective surface. This therefore forms the following etalons: 1) the proximal side of the membrane and the end of the optical fibre; 2) the distal side of the membrane and the end of the optical fibre; 3) the proximal and distal sides of the membrane.

Such a sensor typically involves the detection of nano-metre-scale deformations of the membrane (and/or other fibre-tip structure) by monitoring changes in the phase of the interferogram measured from reflected interrogation light transmitted by the interrogation light guide. In general, these deformations are caused by temperature changes (due to thermal expansion) and/or by a change in external pressure (for example, due to expansion or contraction of a cavity enclosed by the membrane in response to changes in external pressure). Deformation measurements can therefore be processed to obtain changes in temperature and/or in external pressure. These measurements may be calibrated (for example, with respect to other sensors) to obtain absolute temperature and/or pressure measurements.

One or more reflective surfaces in the membrane may be transmissive at some wavelengths and reflective at others, thereby allowing different incident light wavelengths to either pass through or be reflected to varying degrees. There are various ways in which such wavelength-dependent reflectivity may be achieved. For example, the surfaces may comprise dielectric coatings, or they may have integrated chromophores, such as nanoparticles, with wavelength-dependent optical characteristics. Such variations in wavelength sensitivity can be used to select between different modes of operation according to the wavelength of the light source being utilised. For example, excitation light may have a wavelength to pass through the membrane into the surrounding medium in order to heat such medium, while interrogation light at a different wavelength is reflected back from the membrane. In a different mode of operation, the excitation light may have a different wavelength so that it is absorbed within the membrane. Accordingly, absorption of the excitation light will result in heating of the membrane, such as to a predetermined temperature (as determined for example by the measured sizing of the etalon cavity). The excitation light may then be turned off, and the flow rate measured by tracking the contraction of the etalon cavity as the flowing medium (fluid) cools the membrane.

The membrane may be suspended at the distal end of the interrogation light guide, for example, by means of a glass capillary tube that is affixed to the outer distal section of the optical fibre by an adhesive or spliced directly to the distal end of the fibre. Alternatively, the membrane may be held in place by some other structure located at the end of the fibre. The cavity may be formed naturally as a result of a spacing the membrane and the end of the fibre; in other implementations, a cavity may be injected or otherwise moulded into a material at the fibre tip.

In some implementations, the distal end of the interrogation light guide may be provided with a polymer coating (with or without having a gas cavity). For example, the coating may have a dome shape. When formed from some polymeric materials, such as PDMS, a coating with this dome shape is substantially insensitive to changes in pressure at levels relevant to physiological environments due to the high bulk modulus of the material, while remaining sensitive to changes in temperature due to the high linear expansion coefficient of the material. This insensitivity to pressure changes may be utilised to obtain direct temperature measurements which are not impacted by changes in pressure. Note that the dome may also provide additional reflective surfaces (and hence corresponding additional etalons).

A single interrogation light guide can be used to interrogate multiple etalons, providing the etalons formed by each reflective surface and their surrounding structures have sufficiently different optical path lengths to be resolved using the technique of FD-OCT (or any other suitable technique). In some implementations, the multiple membranes may be located at the distal ends of different (respective) optical fibers, which may all be linked to the interrogation light guide. In some implementations, the multiple membranes may be used to provide (simultaneous) pressure, temperature, and flow measurements at different spatial locations along the sensor. For example, these different spatial locations might be proximal and distal to a stenotic region in a vessel. A measurement at a location proximal to a stenotic region could then be used as a reference with which to compare a measurement at a distal location, and also to compute parameters such as the pulse wave velocity. Additionally, temperature measurements at locations proximal and distal to a location at which heating is performed with the excitation light also support measurement of the flow direction.

The sensor described herein may be located within a medical device such as a catheter or a guidewire and used to measure pressure within a physiological vessel, cavity or tissue. For example, the sensor may be placed within a microcatheter that can be inserted over a guidewire used for vascular interventions (typically 0.014 or 0.035 inches in diameter); alternatively, the sensor may be placed within a guidewire. The medical device may include features such as holes or optically transparent regions to allow for excitation light to be provided to the medium, and/or optically absorbing coatings that absorb excitation light and allow for thermal conduction into the flow medium. If the sensor is positioned in a guidewire, the excitation light may be provided directly to the inner surface of the guidewire, which is then in thermal contact with the flow medium.

Measurements of membrane deformation may be calibrated to temperature, which can likewise be measured from changes in specific components in reflected light along the optical fibre. The sensing device may be utilised for the measurement of instantaneous flow by exploiting the heating effect of transmitted excitation light on the surrounding medium. Specific wavelengths of transmitted light may be coupled with dichroic optical absorbers to provide heating to specific components of the surrounding medium, e.g. blood or water. Variations in flow will cause fluctuations in the ambient temperature at the device, and hence corresponding variations in the size or separation of the etalon cavity (or cavities), which are caused by changes in the heating and cooling of the surrounding medium or fluid. This approach can be extended by pulsing the excitation light, thus accentuating the effects of temperature fluctuations.

A spatially averaged measurement of flow can be performed by heating the surrounding medium at a location proximal to the device in a pulsatile manner, for example by warming the surrounding medium by pulsing light at that location. The excitation light can be delivered through a separate fibre or transmitted along the interrogation light guide. Specific wavelengths of light can be used to heat the surrounding medium to provide a temperature increase which is dependent on the composition of specific components within the medium. Interleaving of light pulses of different wavelengths may be used to calculate ratiometric concentrations of separate components within the medium, and calibrated to provide monitoring of absolute values of components within the medium, such as haemoglobin concentration, blood lipids, and haemoglobin oxygenation.

The interrogation light guide and the excitation light guide can also be used to obtain optical measurements of the sensor, the flow medium, or structures in close proximity to the flow medium such as the vessel. For instance, the distal end of the sensor may be provided with compounds with fluorescence that varies in response to changes in temperature, pressure, or chemical composition of the flow medium. A temperature measurement obtained in this way can be used in combination with, or as a replacement of, measurements derived from the changes in optical path length in the sensor. Likewise, the sensor may comprise nanostructures that can be used for surface-enhanced Raman spectroscopy measurements of the flow medium or of the sensor. To maximise signal intensities in fluorescence and Raman spectroscopic measurements, light may be received with multi-mode fibre cores, which can include the excitation light guide or an inner cladding of the interrogation light guide.

FIG. 1 is a schematic diagram of an example of a sensor 100 in accordance with certain implementations of the invention. The sensor 100 (also referred to as a sensor element and/or sensing device) comprises an optical fibre 110 which serves as an interrogation light guide. The optical fibre includes a coating 120 covering the distal end of the optical fibre 110. The coating 120 may be formed, for example, from an elastic polymer having a relatively high linear expansion coefficient, such as polydimethylsiloxane. The coating may be a structure which is manufactured at the distal end of the fibre, or may be cavity injected or otherwise attached or moulded onto the distal end of the fibre 110. The coating 120 has a first reflective surface 130 at the fibre-coating interface and a second reflective surface 140 at the interface between the coating 120 and a cavity 170.

The two surfaces 130, 140 oppose each other, such that they are substantially parallel to one another, both lying in the plane perpendicular to the main longitudinal axis of the optical fibre 110. In other words, the two surfaces are substantially perpendicular to the transmission direction of light in the core of the optical fibre 110. In some examples, the coating 120 may have a curved profile with the second surface 140 forming a (potentially flattened) dome or other rounded shape. In such examples, the two reflective surfaces 130, 140 may then only be parallel in a central region.

The sensor 100 further includes a membrane 125 positioned distal to the coating 120. The membrane 125 has a first reflective surface 135 and a second reflective surface 145, so the sensing device of FIG. 1 includes four reflective surfaces overall. The membrane 125 is affixed to the distal end of the optical fibre 110 using a capillary 115. The (gas) cavity 170 is located proximal to the membrane 125, in other words, between the coating 120 and the membrane 125.

The sensor 100 may be inserted into a vessel (or tube or channel) filled with a medium, such as a fluid. In the example shown, it is assumed that the medium comprises a fluid which is flowing in a direction indicated by arrow 175, which is substantially parallel to the longitudinal axis of the optical fibre 110, and also coincides with the insertion direction of the sensor 100 (the sensor 100 is typically inserted into the vessel with the flow rather than against the flow).

The sensor 100 of FIG. 1 may be integrated into a medical device for the measurement of pressure and/or temperature of the surrounding medium at various locations within a body. For example, the sensor 100 may be incorporated into a very thin device, e.g. a coronary angioplasty guidewire, with a removable optical connector at the proximal end. Another possibility is that the sensor 100 is integrated into an over-the-wire catheter, either a monorail catheter, balloon catheter or sheath catheter, which may be placed into a vessel, organ or lumen.

As illustrated in FIG. 1, the optical fibre 110 is configured to provide interrogation light 150 and excitation light 160 for heating the medium to the distal end of the sensor 100. In other words, the optical fibre 110 of FIG. 1 acts as both an interrogation light guide and as an excitation light guide. The membrane surfaces may be (at least partly) transmissive at some wavelengths and (at least partly) reflective at other wavelengths, therefore allowing different incident light wavelengths to pass through and/or to be reflected as appropriate. In particular, FIG. 1 shows the excitation light 160 generally passing through the membrane 125 into the fluid, while at least some of the interrogation light 150 is reflected back from membrane 125.

Pairs of reflective surfaces, from both the coating 120 and the membrane 125, form respective etalons; for example, one etalon is formed from the pair of reflective surfaces 140, 135. Another etalon is formed from the interrogation light 150 which is reflected at the first and second opposing surfaces 130, 140 of the coating 120. The reflected interrogation light 155 is then be transmitted back through the optical fibre 110 towards the proximal end of the sensor 100. The interrogation light is selected to have a wavelength (or range of wavelengths) appropriate to the spacing of the reflective surfaces for each etalon.

The reflected interrogation light 155 which returns to the proximal end of the optical fibre 110, incorporates an interference pattern (or patterns) resulting from the light being reflected by the etalons. This interference pattern may be spectrally resolved to obtain an interferogram, whereby phase differences in the interferogram are directly related to the optical path length travelled by the interrogation light in each etalon—e.g. based on the separation of the first and second opposing surfaces 130, 140 for the etalon corresponding to coating 120. Furthermore, the thickness of the coating, i.e. the separation of the first and second opposing surfaces 130, 140, is directly proportional to the temperature of the coating 120 according to the coefficient of thermal expansion of the coating material.

To support integration of the sensor 100 into invasive medical devices with wide application, it is important to minimise the lateral dimensions of the sensor as much as possible. The use of a single optical fibre 110 for transmitting both the interrogation light 150 and the excitation light 160, and also for receiving the reflected interrogation light, without requiring any additional components (such as electrical wiring) extending along or through a vessel is very helpful for achieving such small dimension (and can also help to reduce manufacturing complexity).

In the device of FIG. 1, the deflection of the membrane 125 towards or away from the proximal end is dependent on the pressure of the medium. For example, if high pressure is applied to the membrane by the medium or fluid, the cavity is compressed, thereby reducing the optical path between the reflective surfaces 130 and 135 (and also between surfaces 140 and 135, etc).

In the device of FIG. 1, the excitation light 160 is provided, like the interrogation light, through the optical fibre 110. In particular, the excitation light 160 may be transmitted to the distal end of the sensor element 100 to increase the temperature of the surrounding medium, for example, through energy deposition into a component (e.g. an absorbing covering) of the sensor element 100, or directly into the medium surrounding the distal end of the sensor element 100. The use of light transmitted by the optical fibre 110 to provide energy for heating the medium offers various advantages compared with known methods of thermodilution and heat energy deposition. For example, using such an approach, heating may be switched on and off rapidly, without the need for saline injections. Additionally, no electrical power supply or connectors are required at the distal end, and no tracer or infusion needs be performed or administered.

The excitation light 160 may have a wavelength, a set of discrete wavelengths, and/or a range of wavelengths, which is optimal or good for absorption by one or more particular compounds of the medium, for example water or haemoglobin, thereby allowing energy to be directly deposited into the medium. Alternatively (or additionally), an indirect approach may be followed, whereby the excitation light 160 is absorbed by (deposited into) a component at the distal end of the sensor element 100—for example, the membrane 125—which then in turn heats the surrounding medium. Note that in some implementations, at least some the excitation light may enter the medium upstream of the distal end, i.e. offset somewhat towards the proximal end (some examples having such a configuration are discussed below).

In some implementations, the excitation light 160 may have a different wavelength range from the interrogation light 150. For example, the membrane 125 may be configured to be substantially transmissive to wavelengths of the excitation light 160 and reflective to wavelengths of the interrogation light 150. In other examples, the excitation light 160 and the interrogation light 150 may share the same optical source and hence the same range of wavelengths.

The sensor element 100 may be incorporated into a device for performing flow measurements, i.e. to act as a fluid flow sensor for use, for example, in a vessel, tract or lumen. One method of measuring fluid flow using the example sensor element 100 of FIG. 1 comprises depositing thermal energy in the medium at the distal end and subsequently monitoring the rate of cooling. In some implementations, thermal energy (heat) may be provided by delivering the excitation light 160 directly to the medium (or to a surface of the sensor, or of a medical device incorporating the sensor). The excitation light may pass into the medium itself for direct heating of the medium, and/or the sensor may be provided with a surface optimised for converting the excitation light 160 into thermal energy (which is then passed, for example by conduction, into the surrounding medium). The time-resolved change in temperature, as measured with the interferogram, can be calibrated to obtain a measurement of the time-resolved change in flow. If the fluid flow speed changes then the rate of cooling also changes. For example, based on the known light energy delivered by the excitation light 160, together with knowledge of the physical constraints of the sensor and of the fluid/medium undergoing thermal deposition, suitable calculations may be performed, e.g. within a console, see below, to permit calculation of the fluid flow rate (volume and velocity).

The wavelength of the excitation light 160 may be optimised or specifically chosen to provide heating of selective constituents of the medium, such a deoxygenated or oxygenated blood, or water (for example). Measurement of the resulting temperature at the sensor can give information regarding the constituents of the medium (and their relative concentrations)

In some implementations, the excitation light may be pulsed and a flow measurement is obtained from a difference in time between delivery of a heating light pulse and a corresponding change in separation of the first and second opposing surfaces. This approach is particularly appropriate if there is a spatial offset between a first position where the heating occurs, and a second position where the membrane (temperature sensor) is located. In effect, such a configuration provides a flow velocity based on the time taken for the heated liquid to flow the known distance between the first and second positions.

If a pulse of excitation energy is deposited into the medium, the dissipation time for this energy may depend not only on the flow rate, but also on structural (e.g. anatomical) factors. In some cases, an excitation light diffuser may be included in the sensor to optimise energy delivery to the medium. Consequently, temporal changes in the separation of the reflecting surfaces may be processed to obtain information about the vessel geometry or flow characteristics.

In some cases, the excitation light may be modulated, and a flow measurement is obtained from a difference in the temperature of the membrane with the excitation light at two or more intensities. This can help calibrate the temperature and flow rate, since certain factors may cancel out as a result of this subtraction. In a somewhat similar manner, rather than having a fixed excitation light and detecting a variation in the etalon optical path length, another approach is to modulate the excitation light to achieve a substantially constant separation of the reflecting surfaces of the etalon. In this case, the temporal profile of the modulation is analysed to obtain information about the flow characteristics. It will be appreciated that combinations of such implementations may be used simultaneously, including to facilitate internal calibration.

In some cases, pulses of excitation light may be gated (matched or synchronised) to the timing and/or variation of ECG, flow, pressure waveform, or any other suitable physiological measure and/or to the cardiac cycle timing. Such gating may be varied, for example to allow determination of time-gated flow during different components of the cardiac cycle. In a similar manner, the pulse frequency of the excitation light 160 may be modulated, with or without cardiac gating, to prevent inadvertent measurement only at one point or period (phase) within the cardiac cycle. The shape, duration, timing and intensity of such pulses of excitation light may also be varied to optimise measurement characteristics, such as signal-to-noise ratios.

In some cases, the interrogation light guide and/or the excitation light guide also transmits pulsed or modulated light that is absorbed by a component of the medium or the sensor to generate ultrasound. This can be useful for various reasons, such as when using an external ultrasound monitor to locate the sensor, or obtaining some form of ultrasound image or scan of the vicinity of the sensor, etc.

Figure 2:
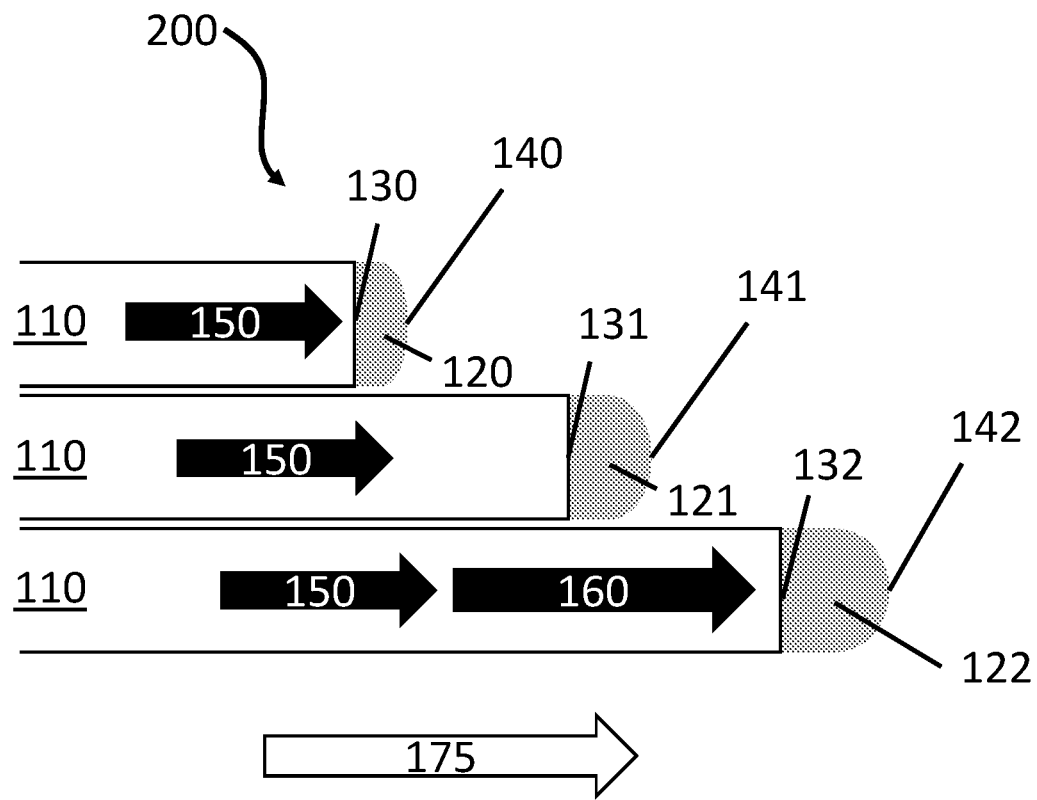
FIG. 2 is a schematic diagram of an example of a sensor as described herein, the sensor including three optical fibres with respective coatings.

FIG. 2 is a schematic diagram of another example of a sensor 200 in accordance with certain implementations of the invention. The sensor 200 of FIG. 2 is formed from three sensor elements, each comprising an optical fibre 110 (or other type of light guide) having a respective coating 120, 121, 122 located at the distal end of the sensor. The interrogation light 150 may be provided by a single interrogation light guide which is split (typically near the distal end) using fibre couplers (not shown) into three optical fibres 110, such that each of coatings 120, 121, 122 is located at the distal end of a respective optical fibre. Each of the coatings 120, 121, 122 provides first and second reflective surfaces 130, 140 (and 131, 141 and 132, 142) substantially as described above for FIG. 1.

Although FIG. 2 indicates the transmission of interrogation light 150 to and from each sensor element, it will be appreciated that the optical fibre of each sensor element may also transmit excitation light 160 (as described above for FIG. 1) to all of the sensor elements, not just coating 122 (as shown in FIG. 2). Furthermore, while FIG. 2 shows a sensor 200 having three sensor elements, other example implementations may have more sensor elements, or may have fewer sensor elements.

The coatings 120, 121, 122 form respective etalons acting at the distal end of each optical fibre 110, each of which is dependent on the temperature of the surrounding medium. Interrogation light 150 passing down each optical fibre is reflected at one or other surface to produce optical interference between the different reflective surfaces (130, 140; 131, 141; 132, 142). This allows an interferogram to be produced, as described above with reference to FIG. 1.

To allow for etalons at the distal end of each optical fibre to be differentiated using FD-OCT, the etalons can be configured to have optical path lengths that are larger than the resolution with which absolute differences in optical path length can be resolved. Consequently, for a given pressure and temperature in the medium (and other relevant parameters), the separation of the opposing reflective surfaces of each coating will differ. Thus in FIG. 2, coating 120 is shown to have the smallest separation between its opposing surfaces 130, 140 while coating 122 is shown to have the largest. The spectrum of the reflected light from each etalon can be monitored and compared with the reflected light from the other two etalons to provide a higher sensitivity for detecting movement of coatings.

Furthermore, the positioning of the coatings 120, 121 and 122 is shown in FIG. 2 as being slightly staggered or offset along the longitudinal axis of the sensor 200. This allows for temperature measurements at different locations in the medium, according to the positional configuration of the various sensor elements in any given implementation.

In some implementations, the coatings 120, 121, 122 shown in FIG. 2 may differ from one another, for example, they may have different structures and/or be composed of different materials and/or have different sensitivities, e.g. to chemical or other stimuli. These differences may, for example, impact the respective dependences of the membranes on the physical parameters of the medium. In this manner, particular membranes may be configured to be dependent primarily on particular stimuli. For example, one etalon may be mechanically designed to be substantially insensitive to changes in bulk pressure in the range −20 to 300 mm Hg (corresponding to typical physiological parameters in a body), whereas one or more other etalons would be sensitive to changes in this range. Accordingly, the former etalons would then be able to provide a calibration point (or control reading) for use with the other etalons in the overall device. In other examples, individual coatings may be sensitive to chemical and/or other stimuli.

Figure 3:
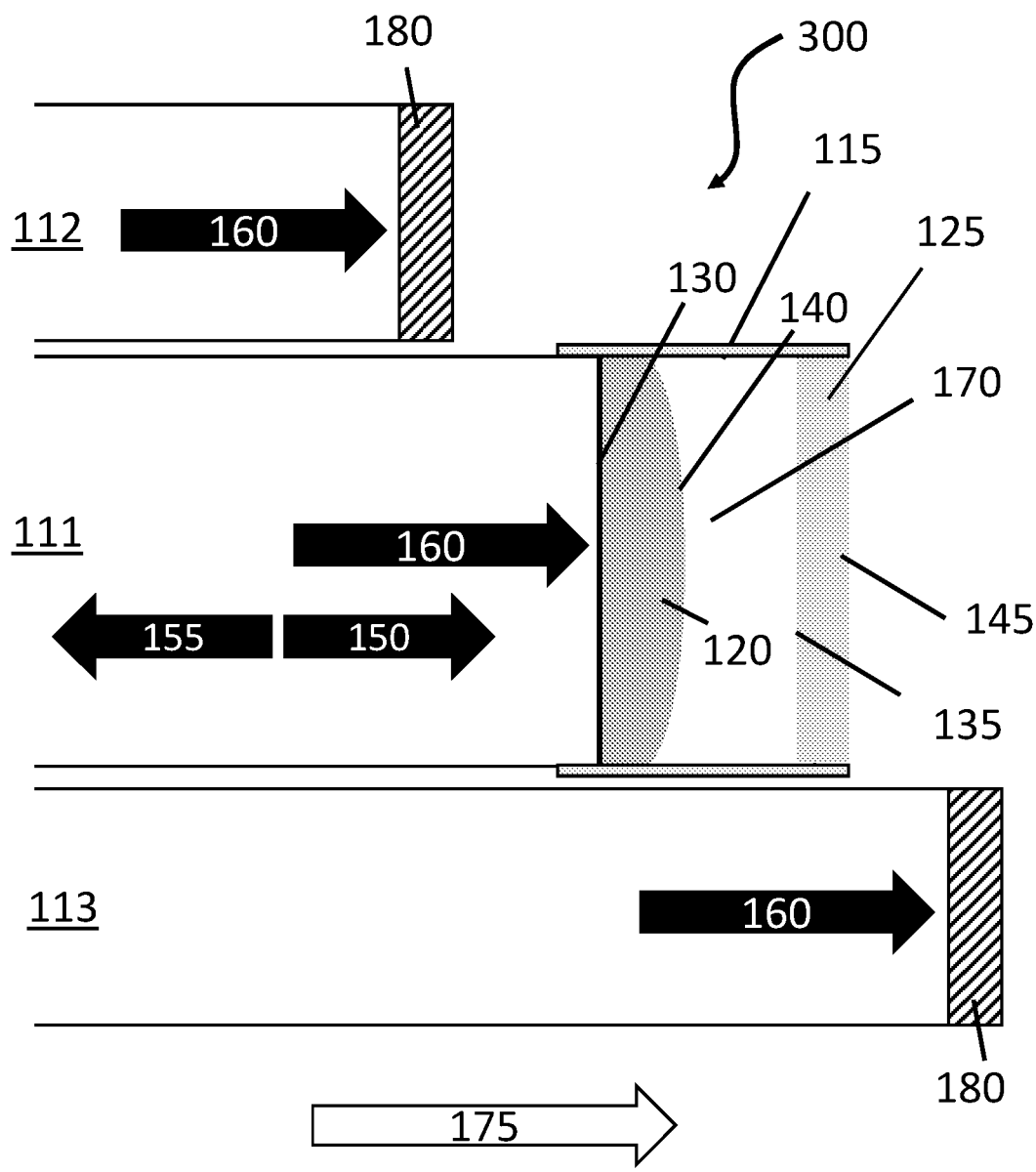
FIG. 3 is a schematic diagram of an example of a sensor as described herein, the sensor including three optical fibres with respective coatings, and the central optical fibre further including a membrane located in a capillary extending from this central optical fibre.

FIG. 3 is a schematic diagram of an example of a sensor 300 in accordance with certain implementations. The sensor 300 of FIG. 3 has three sensor elements located at the ends of respective optical fibres 112, 111, and 113 and having a positional configuration similar to the sensor 200 of FIG. 2, i.e. the ends of the fibres are longitudinally staggered. However, the sensor 300 of FIG. 3 differs from the sensor 200 of FIG. 2 in that for the former, the central optical fibre 111 has both a coating 120 and a membrane 125 at its distal end analogous to the configuration of FIG. 1, whereas the other sensors have a wavelength dependent coating 180 (but no membrane). Interrogation light 150 is transmitted down the central optical fibre 111 of this particular sensor, while the other optical fibres 112, 113 are used to provide excitation light (or the heating therefrom to the medium). (In some implementations, the central fibre 111 may also be provided with one or more coloured coatings, such that there are coloured coatings on all three optical fibres).

In the sensor 300 of FIG. 3, excitation light 160 is transmitted not only via the optical fibre 111 comprising the coating 120, but also via the optical fibres 112, 113. The excitation light 160 is transmitted through the optical fibres 112, 113 and can be used to obtain time-gated flow measurements, for example, using single and/or multiple light pulses. Thus excitation light transmitted through the central optical fibre 111 can be used to obtain a measure of flow immediately surrounding the coating 120, while information obtained by heating the medium through the optical fibres 112 and 113 can be used to measure the directionality and rate of flow. For example, if the flow is in the direction indicated by arrow 175, then transmitting excitation light 160 along optical fibre 112 will result in heating of the coating after a delay time corresponding to the flow speed of the medium (and the distance from the distal end of optical fibre 112 to the distal end of optical fibre 111). On the other hand, transmitting excitation light 160 along optical fibre 113 will result in little or no heating of coating 120, since the warmer fluid will travel downstream, away from the coating 120. However, if the flow direction is the reverse of the arrow 175, then the opposite applies: coating 120 will generally not detect heating caused by excitation light provided along optical fibre 112, but will detect (after a time delay) heating caused by excitation light provided along optical fibre 113.

The coatings shown in FIG. 3 are (at least partly) optically absorbing at some wavelengths and (at least partly) optically transmissive at other wavelengths. Thus by varying the wavelength of excitation light 160, heat can be generated at the coatings 180 (so that it does not depend on the optical properties of the medium) or generated in the medium (so that it does depend on the optical properties of the medium). Also, if optical fibres 112 and 113 are provided with different coatings 180, they might be selectively activated for heating, even if they share a single source of excitation light (by suitably varying the wavelength of the excitation light). This selective heating can be used, for example, to perform the measurements discussed above, in terms of flow-rate and flow directionality. An alternative way to achieve this is for the excitation light 160 to be modulated at different frequencies or more generally with different temporal patterns for each optical fibre 111, 112, 113. This then allows the effects of heating from each fibre to be differentiated by demodulating the time-resolved temperature signal obtained from the reflected interrogation light 155.

In the example sensor 300, the deflection of the membrane 125 is governed by the pressure differential between the medium and the cavity 170. Other configurations of the membrane 125 may include optimisation of this membrane for detection of other physical phenomena, such as impinging ultrasound waves or changes in the chemical composition of the medium. In FIG. 3, the membrane 125 is shown separated from the coating by cavity 170. However, in other configurations a membrane may be formed as another coating on coating 120 (in which case there are only three reflective surfaces, rather than four such as discussed above in relation to FIG. 1).

Figure 4A:
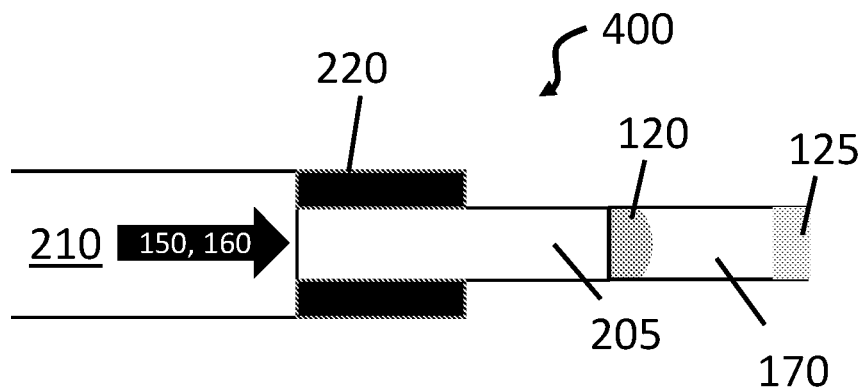
FIG. 4A is a schematic diagram of an example of a sensor as described herein in which the outer cladding of a double clad optical fibre is stripped at the distal end of the sensor and replaced with an optically absorbing layer.

FIG. 4A is a schematic diagram showing an example of a flow sensor 400 in which both excitation light 160 and interrogation light 150 are provided to the distal end of the sensor by a double clad fibre 210. The interrogation light 150 (not shown) is transmitted to a coating 120 and to a membrane 125 which defines a cavity 170 as described above in relation to FIGS. 1-3 using the core to the double clad fibre 210. At the distal end of the double clad fibre 210, the outer cladding is stripped from the fibre and replaced with an optically absorbing layer 220 which is deposited on the inner cladding 205. Advantageously, the refractive index of the optically absorbing layer 220 is higher than that of the inner cladding 205. The excitation light 160 can then exit from the inner cladding 205 into the optically absorbing layer 220, thereby heating the optically absorbing layer 220 and hence heating the surrounding medium. The wavelength of the excitation light 160 may be tuned to help optimise this optical absorption and heat generation in the optically absorbing layer 220 (or to help optimise the heating effect in the surrounding fluid).

Figure 4B:
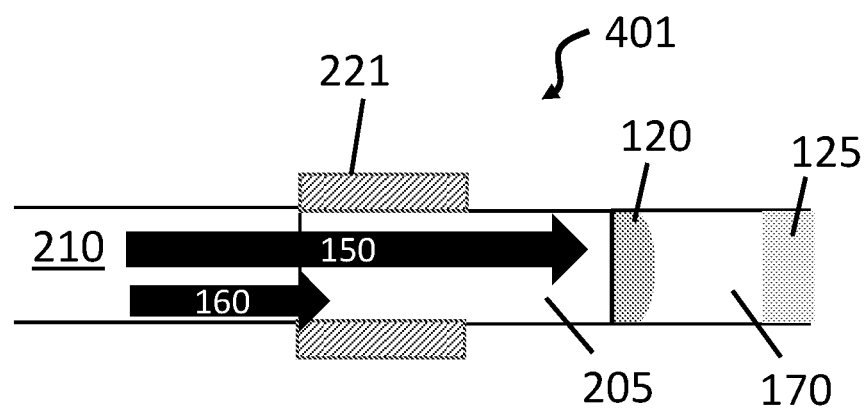
FIG. 4B is a schematic diagram of an example of a sensor as described herein in which a double clad optical fibre is spliced to a single clad fibre that includes a coating to allow excitation light to exit the sensor.

FIG. 4B shows another implementation of a sensor 401; this is generally similar to the sensor of FIG. 4A, but the absorbing layer 220 shown in FIG. 4A is omitted. Instead, in this sensor 401, a double clad fibre 210 is spliced to a single mode fibre 205 with a similar core diameter. The optical fibre is provided with a coating 221 that is substantially transparent to the excitation light 160 and has a higher refractive index than that of the cladding of the single mode fibre 205 to allow the excitation light 160 to exit the sensor 401 and directly heat the medium or a component of the medical device in which the sensor 401 is located.

In some implementations, portions of the coating 221 are provided with an optically reflective layer, confining exit of the excitation light 160 to a defined section or sections of the single mode fibre 205. In other implementations, the coating 221 has a wavelength-dependent optical absorption so that excitation light 160 of one wavelength range is substantially absorbed by the coating 221 while excitation light of another wavelength range is substantially transmitted through the coating 221. In some implementations, the coating 221 includes integrated optical scatterers (not shown in FIG. 4B) to spatially homogenise the excitation which is transmitted through the coating into the medium.

Figure 5:
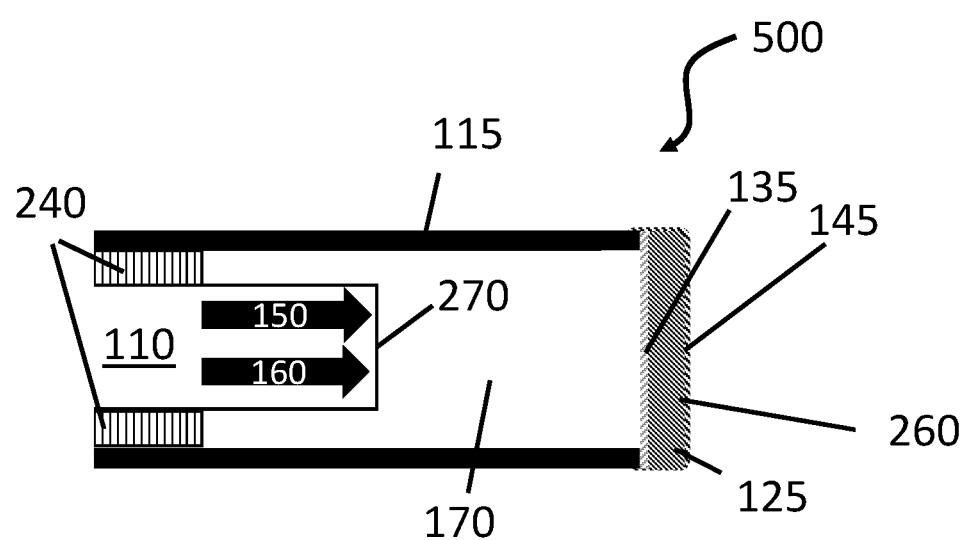
FIGS. 5 to 8 are schematic diagrams of examples of a sensor as described herein including a membrane located in a capillary extending from the optical fibre to form a gas cavity.

FIG. 5 is a schematic diagram showing another example of a sensor 500. In sensor 500, the optical fibre 110 is inserted into and/or affixed to a capillary element 115 (e.g. a glass or metal capillary) with a rigid bonding medium 240, e.g. a heat-cured polymer. One or more layers of elastic, optically reflective material (e.g. a thermoelastic polymer or silicone) may be applied to form a coating of a membrane 125 which is located at the distal end of the capillary 115. The configuration of the sensor 500 thereby creates a gas cavity 170 bounded by the distal end of the optical fibre 110, the capillary 115 and the membrane 120, which may be generally similar to the membranes shown previously FIGS. 1-4B). The membrane 125 of FIG. 5 includes a protective layer 260 to help prevent or reduce degradation of the membrane 125 by the medium. The surface 135 of the membrane 125 facing the optical fibre 110 may also comprise some form of coating, for example, a polymer substance having thermo-expansive properties.

In the sensor 500, the opposing reflective surfaces 135, 145 of the membrane are substantially flat, i.e. perpendicular to the interrogation light 150. The first reflective surface 135 of the membrane is the gas-membrane interface, internal to cavity 170, while the second reflective surface 145 is the membrane-medium interface. Furthermore, in sensor 500 there may also be a reflection at the reflective surface 270 at the optical fibre-gas cavity interface. The configuration of FIG. 5 may therefore provide a first etalon between the surface 270 and the first reflective surface 135 of the membrane 125 (i.e. spanning the gas cavity 170), a second etalon between the first reflective surface 135 and the second opposing reflective surface 145 (spanning the membrane 120), and a third etalon between surface 270 and the second reflective surface 145 of the membrane 125. An interferogram from the first etalon can be used to measure deformation of the membrane 125, which is primarily related to external pressure, while the interferogram from the second etalon can be used to measure any change in the thickness of the membrane 120, which is primarily related to temperature.

The difference in the phases of the frequency components of the interferograms corresponding to the first and third etalons can also be used to measure any change in the thickness of the membrane 125. In conjunction with heating of the medium with excitation light 160 (not shown in FIG. 5), the change in thickness of the membrane 125 and the corresponding change in temperature can be used to obtain flow measurements as described above in relation to FIGS. 1-4B.

The particular sensor 500 shown in FIG. 5 has a capillary element 115 with a diameter that matches the outer diameter of the optical fibre cladding. At the distal end of the optical fibre 110, the outer fibre cladding is stripped away, and the stripped fibre is then inserted into the capillary 115 and affixed by wicking of epoxy 240 or similar glue or material. The outer membrane 125 may be formed by dipping the assembly (of fibre and capillary) into a liquid or gel polymer that forms a membrane on the surface by surface tension and capillary action. Curing of the polymer is then performed as required, e.g. by exposure to UV light, air exposure or heating.

In a further example, the outer diameter of the capillary is similar to that of optical fibre and the capillary is spliced to the distal end of the optical fibre. In further examples, multiple capillaries may be housed within one another, thereby allowing several layers of membranes to be formed. These layers can provide further reflective layers for use in pressure and/or temperature measurement. Additionally some of these membranes may be particularly sensitive to other environmental or physiological parameters of interest, such as for chemical sensing. Sensor 500 may be used in a similar manner to sensor 100, as described above, by application of excitation light 160 to allow heating of the medium. In addition, it will be appreciated that elements of the sensor 500 may be incorporated into the sensors described above in relation to FIGS. 1-4B. For example, the sensor 200 of FIG. 2 may have sensing elements modified to have a membrane 125 and cavity 170 such as shown in FIG. 5 (instead of or in addition to coating 120, 121, 122).

Figure 6:
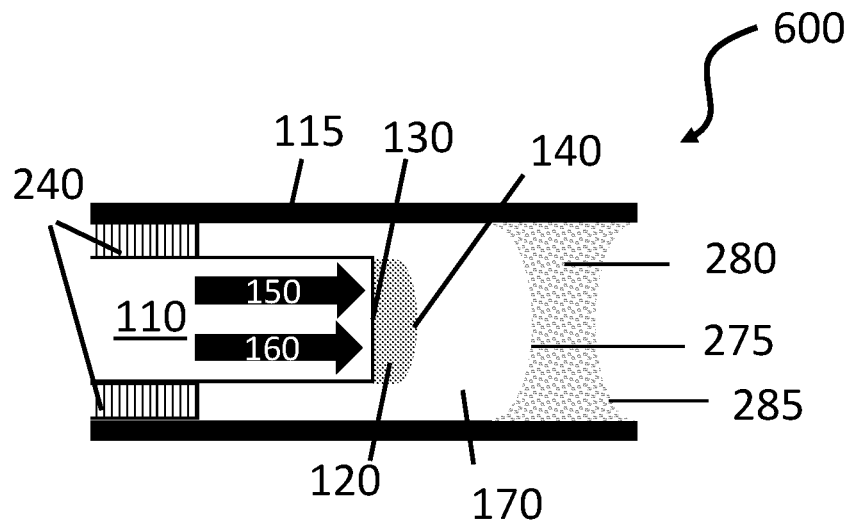

FIG. 6 is a schematic diagram showing another example of a sensor 600 in which measured changes in temperature can be used to determine flow as described above with respect to FIGS. 1-5. As with the example of FIG. 1, sensor 600 includes an optical fibre 110 with a coating 120 that comprises two opposing reflective surfaces 130 and 140 that together form an etalon. The interferogram corresponding to this etalon allows for time-resolved measurements of the separation of the surfaces 130, 140.

As for the example of FIG. 5, the optical fibre 110 is affixed to a capillary 115 by an inflexible bond 240. The capillary 115 extends from the distal end of the optical fibre 110 and supports a membrane 280 which may contain integrated optical scatterers, and which is configured to close off the otherwise open distal end of the capillary 115, thereby forming a gas cavity 170 such as discussed above in relation to FIG. 5. The integrated scatterers, for example, titanium oxide, spatially homogenise excitation light 160 exiting the sensor 600 to help achieve more consistent heating in a larger volume of the medium.

In the example of FIG. 6, the coating 120 may be created by the application of a polymer to the tip of the stripped fibre 110 prior to insertion of the optical fibre 110 into the capillary tube 115. The membrane 280 may then be formed afterwards, in a similar fashion to the formation of membrane 125 as described above in relation to FIG. 5.

In sensor 600, the opposing reflective surfaces 130 and 140 also form etalons with other surfaces in sensor 600. For example, a portion of the interrogation light 150 that is not reflected at the first and second reflective surfaces 130, 140 of the coating 120 is instead reflected from the membrane 280. In particular, the interrogation light is reflected at a third reflecting surface 275 or a fourth reflecting surface 285 of the membrane 280. In sensor 600, the coating 120 may be effectively isolated from the pressure of the medium; therefore the interferogram generated from the reflective surfaces 130, 140 can be used to determine a pressure-independent temperature measurement. In contrast, the separation of the third and fourth reflective surfaces 275, 285 is dependent on both the temperature and the pressure of the medium. (Note that the temperature response of the etalon formed by the first and second reflective surfaces 130, 140 may be slower than the temperature response of the etalon formed by the third and fourth reflective surfaces 275, 285, given that only the latter is in direct thermal contact with the medium; this difference can be modelled or empirically determined, as required).

Figure 7:
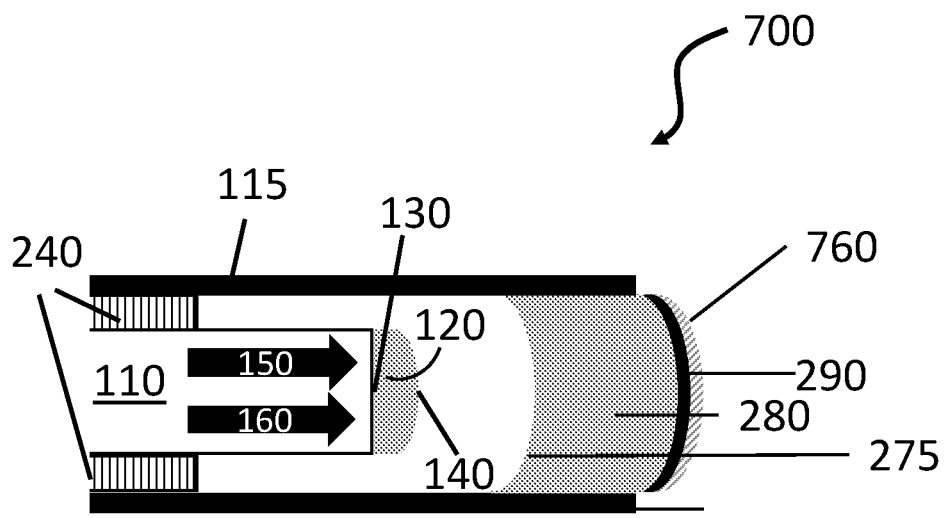

FIG. 7 is a schematic diagram showing another example of a combined temperature and pressure sensor 700 which can be used for measuring flow, as described above. In this implementation, the membrane 280 located at the distal end of the sensor 700 is provided with (i) a reflective layer 290, and (ii) a protective coating 760, both at the distal end. The reflective layer 290 can enhance the amount of interrogation light 150 reflected from what is the most distal reflective surface (and which therefore receives the lowest level of interrogation light). The reflective layer 290 is protected from degradation by the surrounding medium by protective coating 760.

The protective coating may have wavelength-dependent absorption and/or partial reflectivity. In such a device, excitation light 160 in one wavelength range may be absorbed by the protective coating 760 to generate a temperature increase that is then used for flow measurements; in other implementations, the excitation light in another wavelength range may be transmitted by the reflective coating 760 into the medium for use in the flow measurements. Some excitation light 160 that is transmitted into the medium may be reflected from fluid, tissue or material surrounding the sensor 700. The spectrogram of this reflected excitation light can be analysed to provide data relating to e.g. oxygenation of blood, haemoglobin concentration, tissue composition etc.

Figure 8:
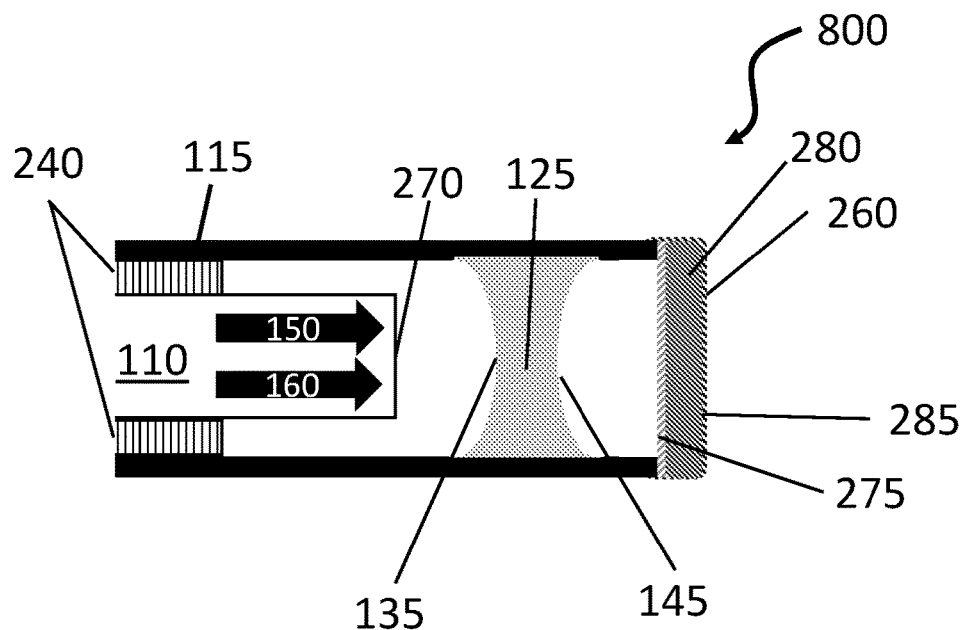
Figure 9:
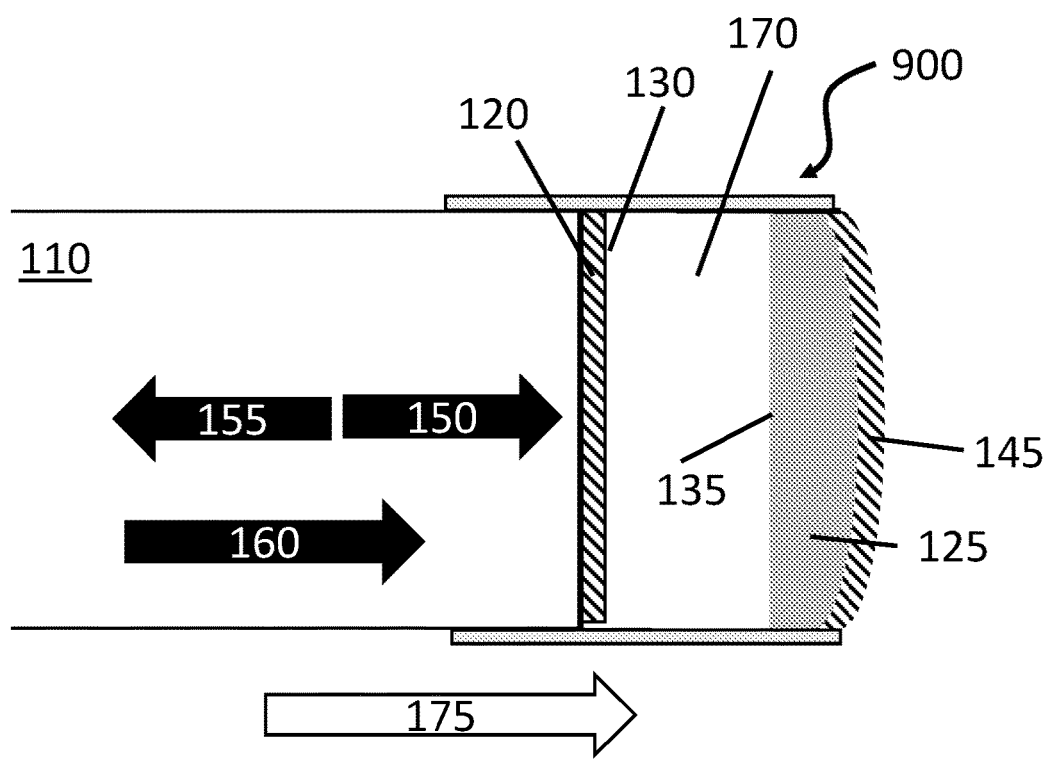
FIG. 9 is a schematic diagram of an example of a sensor as described herein which provides a combined fibre optic temperature/ultrasound sensor.

FIG. 8 shows a further example of a sensor 800. In this example, there is a first membrane 125 which is an intermediate membrane inserted in the capillary 115 between the optical fibre 110 and a second membrane 280. The first membrane 125 is substantially optically transparent and has optically reflective surfaces 135, 145. By varying properties of the first membrane 125 and/or the cavities within the capillary tube 115, the movement of the first membrane 125 can be substantially independent of movement of the second membrane 280. The etalon formed by reflective surface 270 (at the fibre-cavity interface) and reflective surface 275 (the proximal surface of the second membrane 280) can be used to obtain measurements of pressure changes. The etalon formed by reflective surfaces 135, 145 of the first membrane 125 can be used to obtain measurements of temperature changes FIG. 9 is a schematic diagram of a sensor 900 with temperature and ultrasound sensitivity that has a substantially transparent membrane 125 at the distal end of the sensor. The membrane has a reflective surface 135 on its proximal surface and a dielectric reflective surface 145 and on its distal surface. The optical fibre 110 has a dielectric coating 120 on its distal end, with the coating having a distal reflecting surface 130. The two dielectric surfaces 120, 145 have a wavelength-dependent reflectivity, whereby for a first wavelength range, they have a low reflectivity, while for a second wavelength range they have a substantially higher reflectivity, for example, between 70 and 90%. Therefore, for light in the second wavelength range, the etalon formed by the reflective surfaces 130, 145 is a high finesse Fabry-Perot cavity, which can be utilised as an ultrasound receiver in accordance with known technology.

The deformation of membrane 125 is dependent on changes in pressure between the gas cavity 170 and the flow medium, while the expansion or contraction of the membrane 125 is dependent on changes in temperature. Therefore, for interrogation light 150 in the first wavelength range, sensor 900 is able to act as a pressure/temperature/flow sensor, as described above, while for interrogation light 160 in the second wavelength range, sensor 900 is able to act as an ultrasound receiver.

Figure 10:
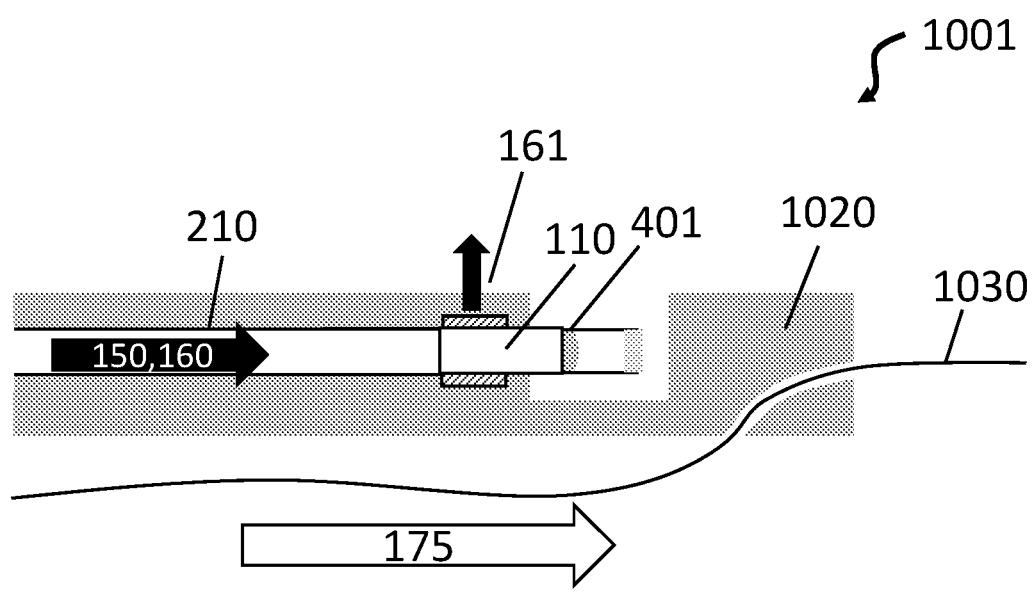
FIG. 10 is a schematic diagram of an example of a sensor as described herein fitted with a guide-wire.

FIG. 10 shows in schematic form a sensor 401 (such as illustrated in FIG. 4B), which allows for pressure, temperature and flow measurements, incorporated into a medical device, in particular a microcatheter 1001 designed for use within the human body. The distal end of the catheter tubing 1020 has holes that allow a guidewire 1030 to pass through the tip of the microcatheter 1001. The microcatheter has a sensor 401 integrated into its lumen. A double clad optical fibre 210, as discussed above, provides excitation light 160 through the inner cladding, and this excitation light is then transmitted through the catheter and into the medium (fluid). Alternatively (or potentially additionally), the microcatheter may contain one or more elements and/or coatings which are optically absorbing and provide conversion of the excitation light to thermal energy, and hence transmission of heat into the medium. The inner core of the fibre 210 provides interrogation light 150 to the pressure/temperature (temp) sensor element at the distal end of sensor 401 as described above.

While FIG. 10 illustrates the incorporation of one particular form of sensor described herein into a microcatheter, the skilled person will recognise that various other forms of sensor described or suggested herein could likewise be incorporated into a microcatheter or other suitable form of medical device. For example, in some implementation, the excitation light 160 may be provided via a second and/or third optical fibre (not shown in FIG. 10, but analogous, for example, to the implementation of FIG. 3).

In some implementations, the sensor 401 may be provided with a nanostructured coating on the distal end to obtain refractive index measurements. Additionally, or alternatively, in some implementations, sensor 401 may utilise frequency modulation of the excitation light 161 for flow measurements. The signal received from the interferogram produced by the interrogation light of sensor 401 can be analysed to detect this frequency modulation, and hence identify the effect of the excitation light.

Figure 11:
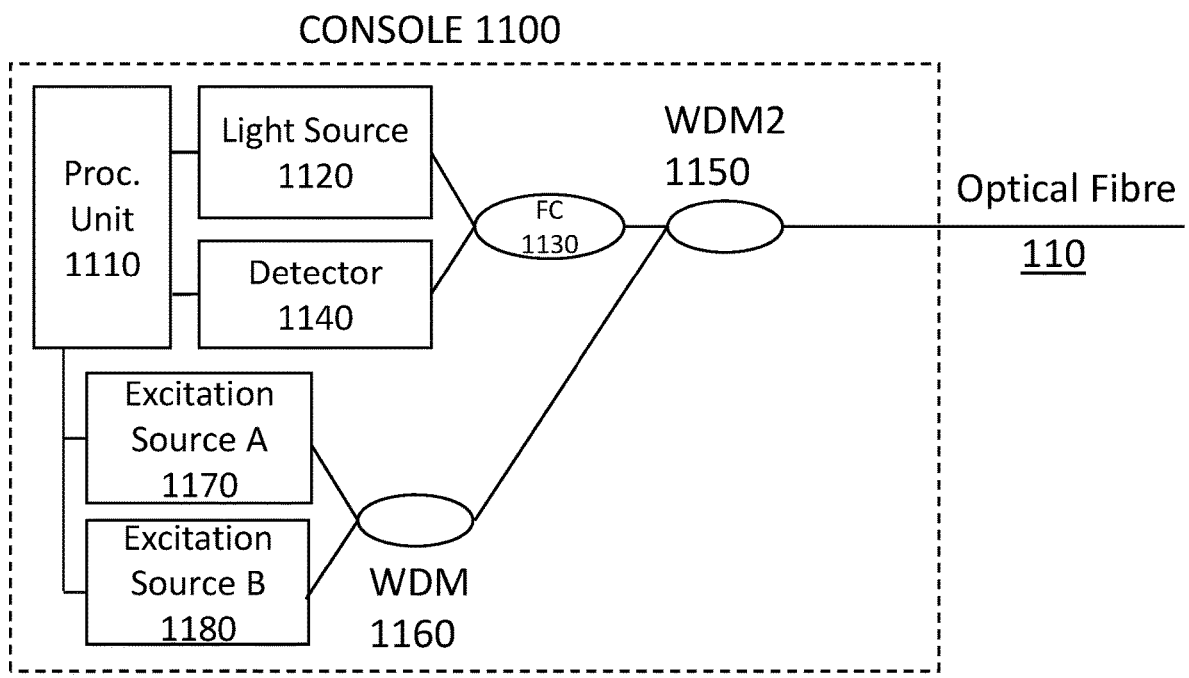
FIG. 11 is a schematic diagram of an example of a console as described herein for use with a sensor, wherein the console provides broadband interrogation light to the sensor.

FIG. 11 is a schematic diagram showing an example of a console 1100 for use with various sensors such as described above. The console 1100 includes a broadband light source 1120 which is linked to the optical fibre 110 acting as the interrogation light guide of the sensor via a fibre coupler 1130. Interrogation light reflected back to the console 1100 from the sensor is wavelength-resolved with a detector 1140, such as a spectrometer, and the resulting signal is then passed to and analysed by a processing unit 1110 such as a computer.

The console 1100 includes two excitation light sources, 1170 and 1180. These two excitation light sources may be modulated at different frequencies, or potentially turned off/on at different time intervals, in order (for example) to apply heat at different locations, such as discussed above in relation to the sensors of FIGS. 2 and 3. In the particular implementation shown in FIG. 11, the two excitation light sources are combined using a first wavelength division multiplexer (WDM) 1160, and are then combined with the interrogation light using a second wavelength division multiplexer (WDM2) 1150. In other implementations, fibre optic couplers may be used to provide excitation and/or interrogation light from the output of WDM 1160 or 1150 (as appropriate) to one or more optical fibres (or other form(s) of light guide), for example, for the implementation shown in FIG. 2.

In some implementations, such as shown in FIGS. 4A and 4B, the interrogation light 150 is delivered and received in the core of a double clad fibre, which therefore serves as the interrogation light guide. The excitation light 160 is delivered in the inner cladding of the same optical fibre (so that the fibre cladding acts as the excitation light guide).

Figure 12:
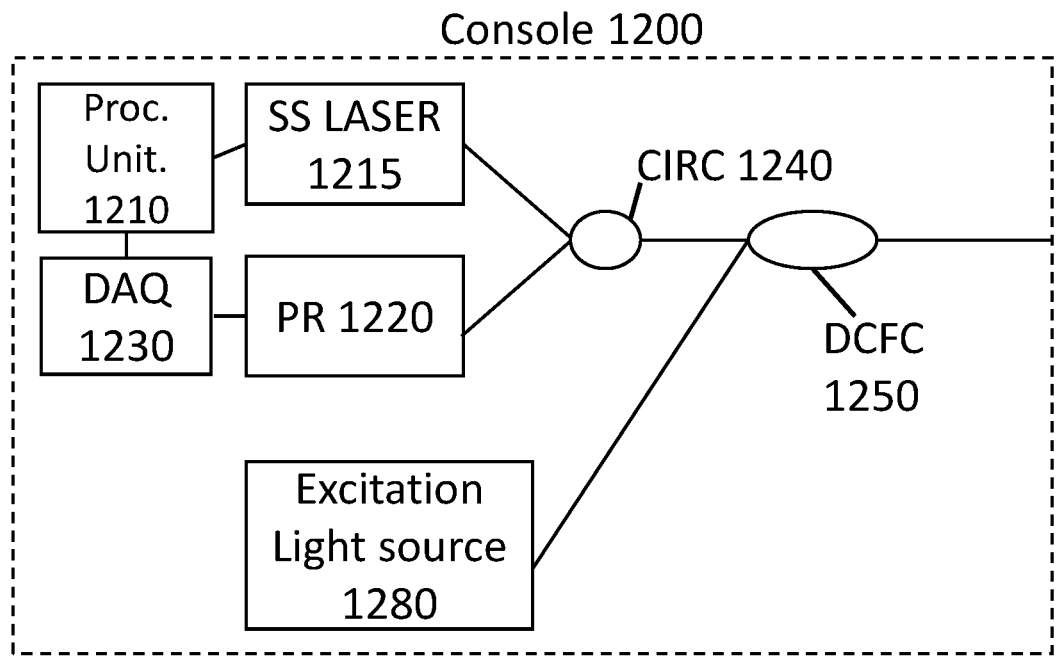
FIG. 12 is a schematic diagram of an example of a console as described herein for use with a sensor, wherein the console provides scanned monochromatic interrogation light to the sensor.

FIG. 12 is a schematic diagram showing an example of a console 1200 that might be utilised with such a double clad fibre. In particular, this console 1200 comprises a swept source laser 1215, which provides interrogation light for forming an interferogram, with the reflected light then being received and measured with a photoreceiver (PR) 1220. The signal from the PR 1220 is provided to the processing unit 1210, such as a computer or other form of analysis system, via a digital acquisition unit (DAQ) 1115. (This implementation uses a photoreceiver rather than a spectroscopic detector because the swept source laser is monochromatic, albeit with a variable wavelength). The console 1200 further includes an optical circulator (CIRC) 1240 which is used to transmit the interrogation light to the sensor, along with a dual clad fibre coupler (DCFC) 1250 for accommodating the interrogation light 150 and the excitation light 160, which is generated from source 1280 on the same (dual clad) optical fibre.

In some implementations, a temperature sensor may be located within the transmission fibre. A feedback mechanism within the console can then be provided to support the modulation of transmission light intensity and/or pulse duration and/or frequency to optimise heating and prevent overheating.

Figure 13:
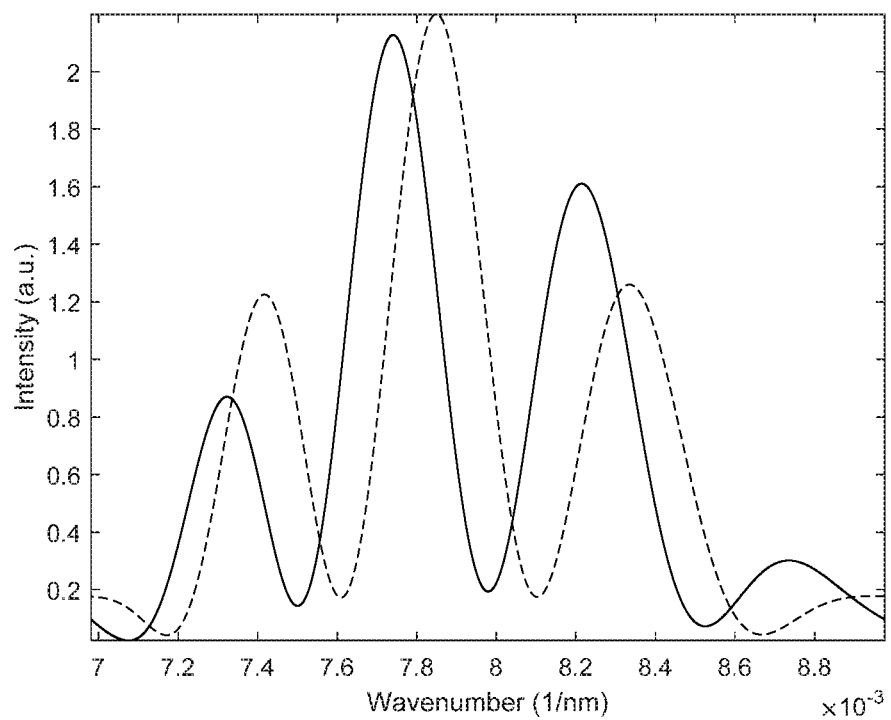
FIG. 13 is an example plot of the spectrographic response (intensity versus wave number) produced by a sensor as described herein.

FIG. 13 shows an example two measured interferograms from two different points in time (one interferogram is shown as a full line, the other as a dashed line), plotted as a function of wave number. Each interferogram comprises a series of peaks and troughs at a particular frequency corresponding to the optical path length of an etalon. These peaks and troughs result from constructive and destructive interference according to the relationship between wavelength and the surface spacing of the etalons. Note that if multiple reflective surfaces are present, then the spectroscopic signal may comprise a superposition of multiple such signals, with each contribution having a frequency indicative of the etalon optical path length.

The two interferograms in FIG. 13 have a phase offset with respect to one another. A phase offset of dP is related to a change in the optical path length of an etalon n·dx with the relationship: $n \cdot dx = \lambda/(4\pi) \cdot dP$, where dx is the change in the length of the etalon, n is the refractive index of the etalon material, and $\lambda$ is the centre wavelength of the interrogation light. The measured temperature change dT is therefore $dT = dL/(\alpha L)$ where L is the length of the etalon and $\alpha$ is the linear thermal expansion coefficient. Accordingly, by measuring this phase offset, the expansions or contraction (and hence the change in temperature) of the membrane can be determined.

Figure 14:
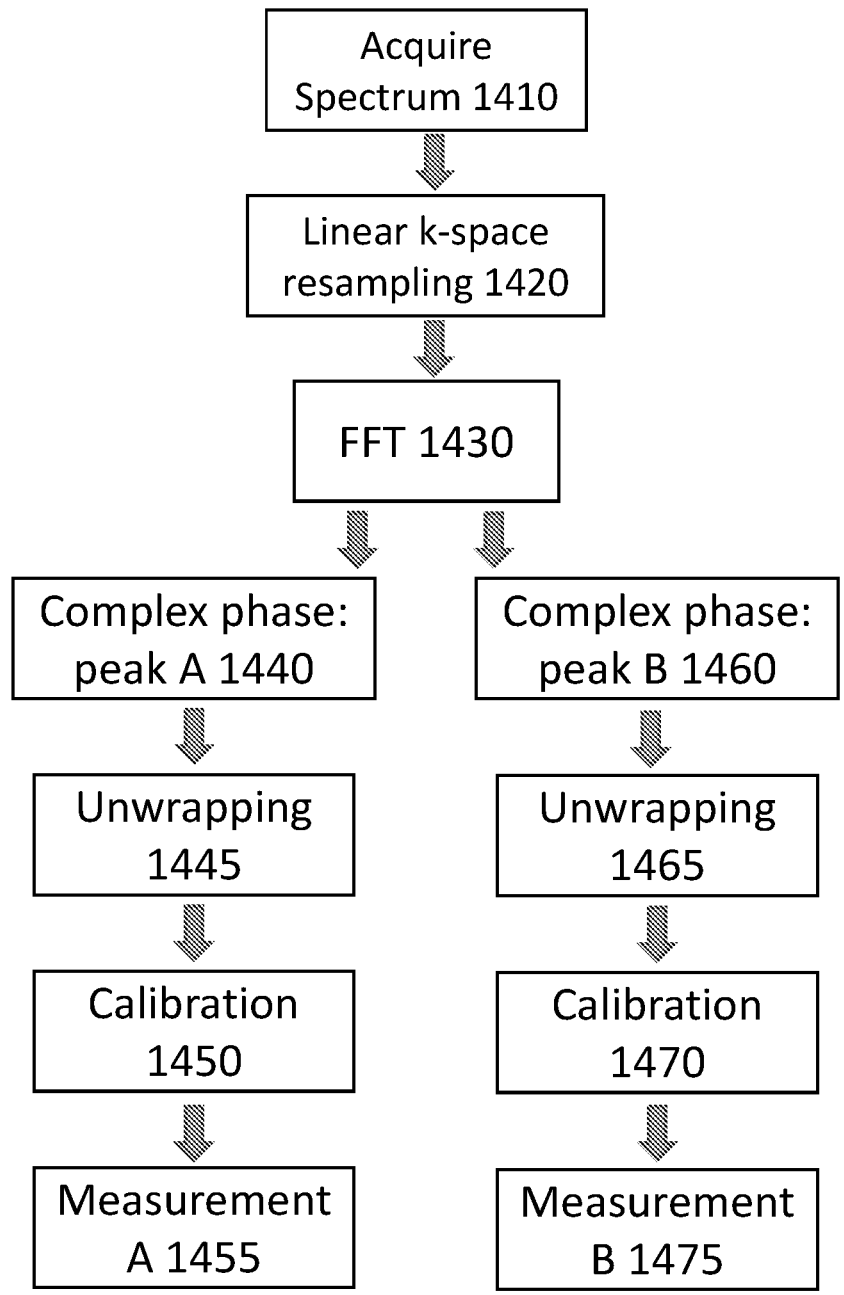
FIG. 14 is a flowchart illustrating a method for analysing spectrographic data such as acquired by a sensor as described herein.

FIG. 14 is a flowchart showing one method of performing such an analysis. The spectrum is acquired 1410, and linear k-space (wave number) resampling is then performed 1420 to obtain an interferogram, on which a fast fourier transform (FFT) 1430 is then performed. In effect, the FFT resolves the interferogram into its frequency components (one of which is shown by the solid line—or dashed line—of FIG. 13). Each peak can be processed separately by phase unwrapping 1445, 1465, calibration 1450, 1470 and measurement 1455, 1475.

Accordingly, the apparatus and methods described herein allow for fibre optic measurements of physical parameters, such as physiological values (e.g. blood flow rate). Other physical parameters that may be measured relate to the concentration of one or more chromophores (which can be determined for example by the amount of heating produced by a given amount of excitation light). A sensor or probe for performing these measurements comprises a deformable structure such a membrane, an optical source for providing interrogation light over an optical light guide for reflection from the deformable structure to create an interference pattern (interferogram) that varies with wavelength and according to the sizing (deformation) of the deformable structure, which in turn varies according to the physical parameter(s) to be measured. In particular, changes in the sizing or deformation of the structure can shift the wavelength or phase of the observed interferogram. The resulting translation in wavenumber can be measured as the difference in the argument of the complex-valued coefficient of the relevant frequency component.

In an example implementation, the fibre is angle-polished and the deformable structure is a polymer, for example, polydimethylsiloxane or polyurethane. The polymer may be positioned within a capillary, such as capillary tube 115 shown in FIG. 5, and the polymer may be drawn into the tube by capillary action. An optically reflective or absorbing layer may be provided in mechanical contact with the deformable structure, for example by depositing ink on the deformable structure. It is understood that such a layer may itself have chemosensitive or thermosensitive properties or otherwise be modified by other physical properties. The reflectance or absorbance of light onto such a layer, or the physical displacement of the membrane to which this layer is applied, can provide a measurement of chemical or physical parameters of the medium.

Deformation of the deformable structure can arise through various types of processes, including: (a) thermal expansion due to heating the deformable structure, (b) application of one or more external forces to the deformable structure; (c) swelling of the deformable structure due to the presence of certain chemicals. An example of the second type of process is a force (pressure) applied by the medium in which the sensor is located. An example of the third type of process is swelling of a polydimethylsiloxane (PDMS) membrane by an organic solvent. More generally for this third type of process, a membrane (or the sub-membrane cavity) placed at the end of the optical fibre(s) may be modified to provide detection of specific chemical phenomena. For example, the membrane or cavity may contain a chemically or osmotically active material that leads to deformation of the membrane or cavity when in contact with variations in concentrations of ions, chemicals or molecules, either by direct deformation, osmosis or thermal expansion.

Note that measurement of heating or temperature can also be used to measure flow rate in a medium, by depositing heat energy into the medium (such as by using excitation light 160), and then timing how long is taken for the heat to dissipate. In some implementations, a device may include multiple sensors (or sensor elements, or reflective surfaces) with differing sensitivities to pressure and temperature, etc. Measurements from these different sensors can be combined to measure various physical parameters of interest. Temporal modulation of the heating (for example, at different rates) can be performed to differentiate contributions from different sources of excitation light 160. In certain situations, a change in the optical path length of an etalon can be induced by both temperature and pressure. A sensor can be configured so that the change in optical path length of an etalon with both temperature and pressure is different for different etalons within the sensor. For example, a first etalon of a sensor having a gas cavity can be highly sensitive to pressure changes, while a second etalon of the sensor may comprise a solid polymer which is (relatively) insensitive to pressure changes and sensitive to temperature changes. As a result, two or more measured changes in optical path length can be combined to disentangle contributions resulting from changes in temperature and pressure.

As mentioned above, for various tasks such as flow measurement, excitation light 160 may be utilised to heat the medium (either directly, or indirectly, by heating a component of the sensor in thermal contact with the medium, such as a portion of the excitation light guide that is optically absorbing for excitation light). The excitation light may be delivered to the medium using the same fibre as that which delivers interrogation light (for example, the excitation light may be provided through the outer cladding of a double clad fibre, and it may be delivered to the medium using a tilted Fibre Bragg grating). In some implementations, the sensor may be provided with a dichroic coating which is substantially reflective to interrogation light but which is substantially transmissive to excitation light delivered to the medium or sample.

In conclusion, various implementations have been described herein, by way of example only, and without limitation. It will be appreciated by the skilled person that features of different implementations can generally be combined with one another to create new implementations. Accordingly, the scope of the application is not restricted to particular examples or implementations described herein, but rather is defined by the appended claims and equivalents.

The invention claimed is:

1. A sensor for measuring a flow of a fluid in a physiological environment, the sensor comprising:
   an interrogation light guide extending from a proximal end to a distal end of the sensor, the interrogation light guide being configured to transmit interrogation light to, and receive reflected interrogation light from, the distal end of the sensor;
   an excitation light guide configured to transmit excitation light to a first position of the sensor, wherein the excitation light is provided for heating the fluid at the first position; and
   a sensing element located at the distal end of the sensor, the sensing element comprising at least two etalons for reflecting interrogation light back along the interrogation light guide towards the proximal end of the sensor, each etalon having a respective optical path length and at least one of the etalons having at least one reflective surface external to the interrogation light guide;
   wherein the sensing element is configured to be in thermal contact with the fluid such that the optical path length of at least one of the etalons is dependent on a temperature of the fluid, and wherein the reflected interrogation light forms an interferogram which is dependent on the optical path lengths of the respective etalons,
   wherein the first position has a proximal distance offset from the distal end of the sensor where the sensing element is located.

2. The sensor of claim 1, wherein different contributions from respective etalons to the interferogram are separable based on interferogram frequency.

3. The method of claim 1, wherein a change in the optical path length of an etalon produces a corresponding change in the phase of the interferogram.

4. The sensor of claim 1, wherein at least two of the etalons are configured to differ in their response to temperature and/or pressure so as to provide separate measurements of temperature and pressure.

5. The sensor of claim 1, wherein the sensor is configured to transmit excitation light into the fluid for direct heating of the fluid.

6. The sensor of claim 1, wherein the sensor further comprises an optically absorbing component configured to receive and absorb the excitation light and to transfer into the fluid heat produced by absorbing the excitation light, wherein the sensor is integrated into a medical device, and wherein the optically absorbing component is part of the medical device.

7. The sensor of claim 1, wherein the sensor further comprises a dichroic coating for selectively transmitting the excitation light into the fluid or reflecting the excitation light within the sensor dependent on the wavelength of said excitation light.

8. The sensor of claim 1, wherein excitation light guide and the interrogation light guide comprise a single light guide which is shared by both the interrogation light and the excitation light.

9. The sensor of claim 1, wherein excitation light guide comprises a cladding of the interrogation light guide.

10. The sensor of claim 1, wherein at least one of the etalons is substantially insensitive to a change in bulk pressure of the fluid in the range −20 to 300 mm Hg.

11. The sensor of claim 1, wherein at least one of the etalons includes a gas cavity, where the sensor further comprises a capillary tube with a membrane closing the distal end of the sensor to form the gas cavity within the capillary tube between the membrane and the distal end of the interrogation light guide.

12. The sensor of claim 1, wherein one etalon comprises a dichroic dielectric coating that provides a low finesse in a first wavelength range corresponding to the interrogation light and provides a high finesse in a second wavelength range for acting as a hydrophone to detect ultrasound waves incident from the fluid onto the sensor.

13. The sensor of claim 1, wherein the sensor is incorporated into a catheter or sheath device for inserting into the body of an animal or human.

14. A system for measuring the flow of a fluid in a physiological environment, the system comprising:
   the sensor of claim 1;
   a first light source for generating the interrogation light;
   a second light source for generating the excitation light; and
   an analysis system for determining the flow from the interferogram.

15. The system of claim 14, wherein the first light source comprises a broadband optical source and wherein the analysis system includes a spectrometer for measuring the interferogram.

16. The system of claim 14, wherein the first light source comprises a wavelength-swept monochromatic optical source and wherein the analysis system includes a photodetector for measuring the interferogram.

17. The system of claim 14, wherein the analysis system determines a time-resolved measurement of flow from changes in the optical path length of at least one etalon during and/or immediately following a time interval in which excitation light is provided.

18. The system of claim 14, wherein the second light source is configured to generate pulsed excitation light, wherein the analysis system is configured to measure the flow based on a difference in time between delivery of an excitation light pulse and a corresponding change in optical path length of at least one etalon.

19. A sensor for measuring a flow of a fluid in a physiological environment, the sensor comprising:
   an interrogation light guide extending from a proximal end to a distal end of the sensor, the interrogation light guide being configured to transmit interrogation light to, and receive reflected interrogation light from, the distal end of the sensor;
   an excitation light guide configured to transmit excitation light to a first position of the sensor, wherein the excitation light is provided for heating the fluid; and
   a sensing element located at the distal end of the sensor, the sensing element comprising at least two etalons for reflecting interrogation light back along the interrogation light guide towards the proximal end of the sensor, each etalon having a respective optical path length and at least one of the etalons having at least one reflective surface external to the interrogation light guide;

wherein the sensing element is configured to be in thermal contact with the fluid such that the optical path length of at least one of the etalons is dependent on a temperature of the fluid, and wherein the reflected interrogation light forms an interferogram which is dependent on the optical path lengths of the respective etalons;

wherein at least one of the etalons includes a gas cavity, where the sensor further comprises a capillary tube with a membrane closing the distal end of the sensor to form the gas cavity within the capillary tube between the membrane and the distal end of the interrogation light guide.

20. A sensor for measuring a flow of a fluid in a physiological environment, the sensor comprising:

an interrogation light guide extending from a proximal end to a distal end of the sensor, the interrogation light guide being configured to transmit interrogation light to, and receive reflected interrogation light from, the distal end of the sensor;

an excitation light guide configured to transmit excitation light to a first position of the sensor, wherein the excitation light is provided for heating the fluid; and a sensing element located at the distal end of the sensor, the sensing element comprising at least two etalons for reflecting interrogation light back along the interrogation light guide towards the proximal end of the sensor, each etalon having a respective optical path length and at least one of the etalons having at least one reflective surface external to the interrogation light guide;

wherein the sensing element is configured to be in thermal contact with the fluid such that the optical path length of at least one of the etalons is dependent on a temperature of the fluid, and wherein the reflected interrogation light forms an interferogram which is dependent on the optical path lengths of the respective etalons;

wherein one etalon comprises a dichroic dielectric coating that provides a low finesse in a first wavelength range corresponding to the interrogation light and provides a high finesse in a second wavelength range for acting as a hydrophone to detect ultrasound waves incident from the fluid onto the sensor.

* * * * *